US009603971B2

(12) United States Patent
Kaplan et al.

(10) Patent No.: US 9,603,971 B2
(45) Date of Patent: Mar. 28, 2017

(54) SILK-BASED IONOMERIC COMPOSITIONS

(75) Inventors: David L. Kaplan, Concord, MA (US); Monica A. Serban, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/582,903

(22) PCT Filed: Mar. 4, 2011

(86) PCT No.: PCT/US2011/027153
§ 371 (c)(1),
(2), (4) Date: Oct. 31, 2012

(87) PCT Pub. No.: WO2011/109691
PCT Pub. Date: Sep. 9, 2011

(65) Prior Publication Data
US 2013/0039986 A1 Feb. 14, 2013

Related U.S. Application Data
(60) Provisional application No. 61/311,070, filed on Mar. 5, 2010.

(51) Int. Cl.
A61L 27/52 (2006.01)
A61K 9/08 (2006.01)
A61K 9/50 (2006.01)
A61L 15/26 (2006.01)
A61L 15/32 (2006.01)
A61L 27/18 (2006.01)
A61L 27/22 (2006.01)
A61L 27/26 (2006.01)
A61L 27/50 (2006.01)
A61L 27/54 (2006.01)
A61L 15/42 (2006.01)

(52) U.S. Cl.
CPC ............ *A61L 27/52* (2013.01); *A61K 9/5063* (2013.01); *A61L 15/26* (2013.01); *A61L 15/32* (2013.01); *A61L 15/42* (2013.01); *A61L 27/18* (2013.01); *A61L 27/227* (2013.01); *A61L 27/26* (2013.01); *A61L 27/50* (2013.01); *A61L 27/54* (2013.01); *A61L 2300/00* (2013.01); *Y10T 428/2982* (2015.01)

(58) Field of Classification Search
None
See application file for complete search history.

(56) References Cited

U.S. PATENT DOCUMENTS

| | | |
|---|---|---|
| 1,989,005 A | 1/1935 | Fink et al. |
| 4,233,212 A | 11/1980 | Otoi et al. |
| 4,820,418 A | 4/1989 | Hirotsu et al. |
| 5,047,507 A | 9/1991 | Buchegger et al. |
| 5,245,012 A | 9/1993 | Lombari et al. |
| 5,290,494 A | 3/1994 | Coombes et al. |
| 5,589,167 A | 12/1996 | Cleland et al. |
| 5,606,019 A | 2/1997 | Cappello |
| 5,728,810 A | 3/1998 | Lewis et al. |
| 5,770,193 A | 6/1998 | Vacanti et al. |
| 5,994,099 A | 11/1999 | Lewis et al. |
| 6,110,590 A | 8/2000 | Zarkoob et al. |
| 6,123,819 A | 9/2000 | Peeters |
| 6,175,053 B1 | 1/2001 | Tsubouchi |
| 6,592,623 B1 | 7/2003 | Bowlin et al. |
| 6,815,427 B2 | 11/2004 | Tsubouchi et al. |
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,842,780 B2 | 11/2010 | Kaplan et al. |
| 7,960,509 B2 | 6/2011 | Kaplan et al. |
| 8,071,722 B2 | 12/2011 | Kaplan et al. |
| 8,206,774 B2 | 6/2012 | Kaplan et al. |
| 8,293,486 B2 | 10/2012 | Kaplan et al. |

(Continued)

FOREIGN PATENT DOCUMENTS

| | | |
|---|---|---|
| CA | 2405850 | 10/2002 |
| EP | 1440088 | 7/2004 |

(Continued)

OTHER PUBLICATIONS

Agarwal et al., Journal of Applied Polymer Science, 63(3):401-410 (1997). "Effect of Moisture Absorption on the Thermal Properties of Bombyx mori Silk Fibroin Films."
Altman et al., Biomaterials, 24:401-416 (2003). "Silk-based biomaterials."
Ando et al, Reports on Progress in Polymer Physics in Japan, XXIII:775-778 (1980). "Piezoelectric and Related properties of Hydrated Silk Fibroin."
Asakura et al., Macromolecules, 17:1075-1081 (1984). NMR of silk fibroin 2. 13C NMR study of the chain dynamics and solution structure of Bombyx mori silk fibroin.
Asakura et al., Macromolecules, 18:1841-1845 (1985). "Conformational characterization of B. mori silk fibroin in the solid state by high-frequency 13C cross polarization-magic angle spinning NMR, X-ray diffraction and infrared spectroscopy."
Chen et al., J Appl Polymer Sci, 65:2257-2262 (1997). "pH sensitivity and ion sensitivity of hydrogels based on complex-forming chitosan/silk fibroin interpenetrating polymer network."

(Continued)

Primary Examiner — Jessica Worsham
(74) Attorney, Agent, or Firm — Brenda Herschbach Jarrell; Brian E. Reese; Choate, Hall & Stewart LLP

(57) ABSTRACT

Disclosed herein are pH-dependent silk fibroin-based ionomeric compositions and colloids, and methods of making the same. The state of the silk fibroin ionomeric compositions is reversible and can transform from a gel-like colloid to a more fluid-like solution, or vice versa, upon an environmental stimulus, e.g., pH. Thus, the silk-based ionomeric compositions and colloids can be applied in various industries, ranging from electronic applications to biomedical applications, such as sensors, gel diodes, absorbent materials, drug delivery systems, tissue implants and contrast agents.

22 Claims, 10 Drawing Sheets

(56) References Cited

U.S. PATENT DOCUMENTS

| | | |
|---|---|---|
| 2002/0028243 A1 | 3/2002 | Masters |
| 2003/0007991 A1 | 1/2003 | Masters |
| 2003/0091647 A1 | 5/2003 | Lewis et al. |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0260706 A1 | 11/2005 | Kaplan et al. |
| 2006/0159837 A1* | 7/2006 | Kaplan et al. ........... 427/2.1 |
| 2007/0187862 A1 | 8/2007 | Kaplan et al. |
| 2007/0212730 A1 | 9/2007 | Vepari et al. |
| 2008/0085272 A1 | 4/2008 | Kaplan et al. |
| 2008/0293919 A1 | 11/2008 | Kaplan et al. |
| 2009/0123509 A1 | 5/2009 | Berkland et al. |
| 2009/0171467 A1 | 7/2009 | Mann et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0292338 A1 | 11/2010 | Rheinnecker et al. |
| 2011/0046686 A1 | 2/2011 | Kaplan et al. |
| 2011/0076384 A1 | 3/2011 | Cannizzaro et al. |
| 2011/0121485 A1 | 5/2011 | Rheinnecker et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |
| 2012/0171770 A1 | 7/2012 | Numata et al. |

FOREIGN PATENT DOCUMENTS

| | | |
|---|---|---|
| GB | 1182153 | 2/1970 |
| JP | 55-139427 | 10/1980 |
| JP | 58-38449 | 8/1983 |
| JP | 60-142259 | 7/1985 |
| JP | 60-259677 | 12/1985 |
| JP | 01118544 | 11/1989 |
| JP | 04-263611 | 9/1992 |
| JP | 06-346314 | 12/1994 |
| JP | 08-295697 | 11/1996 |
| JP | 10-36676 | 2/1998 |
| JP | 2000-273264 | 10/2000 |
| JP | 2003192807 | 7/2003 |
| JP | 2004068161 | 3/2004 |
| WO | WO-97/08315 A1 | 3/1997 |
| WO | 99/01089 | 1/1999 |
| WO | 01/36531 | 5/2001 |
| WO | 01/56626 | 8/2001 |
| WO | 02/072931 | 9/2002 |
| WO | 03/022909 | 3/2003 |
| WO | 03/038033 | 5/2003 |
| WO | 2004/000915 | 12/2003 |
| WO | 2004/041845 | 5/2004 |
| WO | 2005/012606 | 2/2005 |
| WO | 2005/123114 | 12/2005 |
| WO | 2008/127405 | 10/2008 |
| WO | WO-2008/127401 A2 | 10/2008 |
| WO | 2009/156226 | 12/2009 |
| WO | WO-2010/057142 A2 | 5/2010 |
| WO | 2011/006133 | 1/2011 |
| WO | WO-2011/011347 A2 | 1/2011 |

OTHER PUBLICATIONS

Chen et al., J Appl Polymer Sci, 73:975-980 (1999). "Separation of alcohol-water mixture by pervaporation through a novel natural polymer blend membrane-chitosan/silk fibroin blend membrane."

Chen et al., Proteins: Structure, Function, and Bioinformatics, 68:223-231 (2007). "Conformation transition kinetics of Bombyx mori silk protein."

Database WPI Week 198205, Derwent Publications Ltd., London, GB AN 1982-09092E & JP 56 166235 A Dec. 21, 1981. Abstract.

Demura et al., Biosensors, 4:361-372 (1989). "Immobilization of biocatalysts with Bombyx mori silk fibroin by several kinds of physical treatment and its application to glucose sensors."

Demura et al., J Membrane Science, 59:32-52 (1991). "Porous membrane of Bombyx mori silk fibroin: structure characterization, physical properties and application to glucose oxidase immobilization."

Derwent Record, Abstract of JP 08295697 A2 "Production of aqueous solution of silk fibroin at high concentration." Nov. 12, 1996.

Doshi et al. J Electrostatics, 35:151-160 (1995). "Electrospinning process and applications of electrospun fibers."

Freddi et al., J Appl Polymer Sci, 56:1537-1545 (1995). "Silk fibroin/cellulose blend films: preparation, structure, and physical properties."

Hijirida et al., Biophysical Journal, 71:3442-3447 (1996). "13C NMR of Nephila clavipes major ampullate silk gland."

Hinman et al., TIBTECH, 18:374-379 (2000). "Synthetic spider silk: a modular fiber."

Horan et al., Biomaterials, 26:3385-3393 (2005). "In vitro degradation of silk fibroin."

Hu et al., Biomacromolecules, 12:1686-1696 (2011). "Regulation of Silk Material Structure by Temperature-Controlled Water Vapor Annealing."

Huang et al., J Biomater Sci Polymer Edn, 12(9):979-993 (2001). "Engineered collagen-PEO nanofibers and fabrics."

Huang et al., Macromolecules, 33:2989-2997 (2000). "Generation of synthetic elastin-mimetic small diameter fibers and fiber networks."

Jin et al., Biomacromolecules, 3:1233-1239 (2002). "Electrospinning Bombyx mori silk with poly(ethylene oxide)."

Jin et al., Adv. Funct. Mater., 15:1241-1247 (2005). "Water-Stable Silk Films with Reduced β-Sheet Content."

Jin et al., Nature, 424:1057-1061 (2003). "Mechanism of silk processing in insects and spiders."

Kim et al., Biomacromolecules, 5:786-792 (2004). "Structure and Properties of Silk Hydrogels."

Kweon et al., J Appl Polymer Sci, 80:1848-1853 (2001). "Preparation of semi-interpenetrating polymer networks composed of silk fibroin and poly(ethylene glycol) macromer."

Lazaris, Science, 295:472-476 (2002). "Spider silk fibers spun from soluble recombinant silk produced in mammalian cells."

Li et al., Biomaterials, 27:3115-3124 (2006). "Electrospun Silk-BMP-2 scaffolds for bone tissue engineering."

Liang et al., J Appl Polymer Sci, 45:1937-1943 (1992). "Improvements of the physical properties of fibroin membranes with sodium alginate."

Lu et al., Acta Biomater. 6(4):1380-1387 (2010). "Water-Insoluble Silk Films with Silk I Structure."

Megeed et al., Pharmaceutical Research, 19(7):954-959 (2002). "Controlled release of plasmid DNA from a genetically engineered silk-elastinlike hydrogel."

Nazarov et al., Biomacromolecules, 5:718-726 (2004). "Porous 3-D Scaffolds from Regenerated Silk Fibroin."

Petrini et al., Journal of Materials Science: Materials in Medicine, 12:849-853 (2001). "Silk fibroin-polyurethane scaffolds for tissue engineering."

Reneker et al., Nanotechnology, 7:216-223 (1996). "Nanometre diameter fibres of polymer, produced by electrospinning."

Sawyer et al., JAMA, 191(9):740-742 (1965). "Dextran therapy in thrombophlebitis." Abstract.

Sofia et al., Journal of Biomedical Materials Research, 54(1):139-148 (2001). "Functionalized silk-based biomaterials for bone formation."

(56) References Cited

OTHER PUBLICATIONS

U.S. Appl. No. 60/906,509, filed Mar. 13, 2007 by Omenetto et al.
U.S. Appl. No. 61/224,618, filed Jul. 10, 2009 by Numata et al.
Wang et al., Langmuir, 21:11335-11341 (2005). "Biomaterial coatings by stepwise deposition of silk fibroin."
Yamada et al., Thin Solid Films, 440:208-216 (2003). "AFM observation of silk fibroin on mica substrates: morphologies reflecting the secondary structures."
Zhou et al., Chem Commun, 2518-2519 (2001). "Preparation of a novel core-shell nanostructured gold colloid-silk fibroin bioconjugate by the protein in situ redox technique at room temperature."
Gupta et al., "Fabrication and characterization of silk fibroin-derived curcumin nanoparticles for cancer therapy", Int J Nanomedicine, 4:115-22. Epub 2009 (2009).
Kaplan et al., "Silk: Biology, Structure, Properties, and Genetics", in ACS Symposium Series, vol. 544, 2-16, Dec. 3, 1993, (McGrath & Kaplan, eds., Birkhauser, Boston, MA,).
Lawrence et al., "Silk film biomaterials for cornea tissue engineering", Biomaterials, 30(7):1299-308, Epub 2008. (2009).
Murphy A. R. et al., "Modification of silk fibroin using diazonium coupling chemistry and the effects on hMSC proliferation and differentiation", Biomaterials, 29(19):2829-38, (2008). Epub Apr. 15, 2008.
L. Shi and C. Berkland; "pH-Triggered Dispersion of Nanoparticle Clusters" Advanced Materials vol. 18, Issue 17, pp. 2315-2319, Sep. 2006.
Shi, L. & Berkland, C. "Acid-Labile Polyvinylamine Micro- and Nanogel Capsules", Macromolecules, 40 (13):4635-4643, (2007).
Soffer et al., "Silk-based electrospun tubular scaffolds for tissue-engineered vascular grafts", J. Biomater Sci Polym Ed., 19(5):653-64, (2008).
Wang et al., "Growth factor gradients via microsphere delivery in biopolymer scaffolds for osteochondral tissue engineering", J. Controlled Release, 134(2):81-90 (2009), Epub Nov. 17, 2008.
Q. Wang, L. Wang, M.S. Detamore, C. Berkland; "Biodegradable Colloidal Gels as Moldable Tissue Engineering Scaffolds" Advanced Materials vol. 20, Issue 2, pp. 236-239, Jan. 2008.
Wang et al., "Sonication-induced gelation of silk fibroin for cell encapsulation", Biomaterials, 29(8):1054-64, (2008), Epub Nov. 26, 2007.
Wang et al., "In vivo degradation of three-dimensional silk fibroin scaffolds", Biomaterials, 29(24-25):3415-28, (2008), Epub May 27, 2008.
Wenk et al., "Silk fibroin spheres as a platform for controlled drug delivery", J. Controlled Release, 132(1):26-34, (2008), Epub Aug. 19, 2008.
Wilz et al., "Silk polymer-based adenosine release: therapeutic potential for epilepsy", Biomaterials, 29(26):3609-16, (2008), Epub Jun. 2, 2008.
Kaplan et al., "Silk", Protein Based Mats. 103-31 (McGrath & Kaplan, eds., Birkhauser, Boston, MA, 1997).
Hofmann et al., "Silk fibroin as an organic polymer for controlled drug delivery", J. Controlled Release,111 (1-2):219-27, (2006), Epub Feb. 3, 2006.
Jin et al., "Electrospinning Bombyx mori silk with poly(ethylene oxide)", Biomacromolecules, 3(6):1233-9, (2002).
Sofia et al., "Functionalized silk-based biomaterials for bone formation", J. Biomed Mater Res., 54(1):139-48, (2001).
Sohn et al., "Phase Behavior and Hydration of Silk Fibroin", Biomacromolecules, 5:751-57, (2004).
Um et al., "Structural characteristics and properties of the regenerated silk fibroin prepared from formic acid", Int J Biol Macromol, 29(2):91-7, (2001).
Wang et al., "Silk microspheres for encapsulation and controlled release", J. Controlled Release, 117(3):360-70, (2007), Epub Nov. 30, 2006.
Wang et al., "Stem cell-based tissue engineering with silk biomaterials", Biomaterials, 27(36):6064-82, (2006), Epub Aug. 7, 2006.
Hachisu, et al., "Preparation of Silk-Like Fibers Designed by Self-Assembled Ionic Polypeptides," Macromol. Biosci. 2003, 3, 92-99.
Itoh, et al., "Reinvestigation on the Buildup Mechanism of Alternate Multilayers Consisting of Poly(L-glutamic acid) and Poly(L-,D-, and DL-lysines)," Langmuir 2008, 24, 13426-13433.
Malay, et al., "pH- and Electro-Responsive Characteristics of Silk Fibroin-Hyaluronic Acid Polyelectrolyte Complex Membranes," International Journal of Pharmaceutics 380 (2009) 120-126.
Numata, et al., "Bioengineered Silk Protein-Based Gene Delivery Systems," Biomaterials 30 (2009) 5775-5784.
Serban, et al., "pH-Sensitive Ionomeric Particles Obtained via Chemical Conjugation of Silk with Poly(amino acid)s," Biomacromolecules 2010, 11, 3406-3412.
Wang, et al., "Nanolayer Biomaterial Coatings of Silk Fibroin for Controlled Release," Journal of Controlled Release 121 (2007) 190-199.
Asakura, T. et al., Structural role of tyrosine in Bombyx mori silk fibroin, studied by solid-state Nmr and molecular mechanics on a model peptide prepared as silk I and II, Magnetic Resonance Chemistry, 42:258-266 (2004).
Bidros, D.S. and Vogelbaum, M.A., Novel drug delivery strategies in neuro-oncology, Neurotherapeutics, 6:539-546 (2009).
Bini, E. et al., Mapping domain structures in silks from insects and spiders related to protein assembly, Journal of Molecular Biology, 335:27-40 (2004).
Lee, E.S. et al., Recent progress in tumor pH targeting nanotechnology, Journal of Controlled Release, 132:164-170 (2008).
Shu, X.Z. et al., Disulfide Cross-Linked Hyaluronan Hydrogels, Biomacromolecules, 3(6):1304-1311 (2002).
Tanaka, K. et al., Determination of the site of disulfide linkage between heavy and light chains of silk fibroin produced by Bombyx mori, Biochimica et Biophysica Acta, 1432:92-103 (1999).
Van Sluis, R. et al., In vivo imaging of extracellular pH using 1H MRSI, Magnetic Resonance Medicine, 41:743-750 (1999).
Zhou, C.Z. et al., Silk fibroin: structural implications of a remarkable amino acid sequence, Proteins, 44(2):119-122 (2001).
International Search Report for PCT/US2011/027153, 5 pages (Dec. 20, 2011).
Lucas, F. et al., The Silk Fibroins, Advances in Protein Chemistry, 13:107-242 (1958).
Written Opinion for PCT/US2011/027153, 5 pages (Dec. 20, 2011).
Perry, H. et al., Nano- and Micropatterning of Optically Transparent, Mechanically Robust, Biocompatible Silk Fibroin Films, Advanced Materials. 20:3070-3072 (2008).

* cited by examiner

SILK-BASED IONOMERIC COMPOSITIONS

CROSS-REFERENCE TO RELATED APPLICATIONS

This application is a 35 U.S.C. §371 National Stage Entry Application of International Application No. PCT/US2011/027153, filed Mar. 4, 2011, which designates the U.S., and which claims benefit under 35 U.S.C. §119(e) of U.S. Provisional Application No. 61/311,070, filed Mar. 5, 2010, the contents of which are incorporated herein by reference in their entirety.

GOVERNMENT SUPPORT

This invention was made with government support under grant EB002520 awarded by the National Institutes of Health. The U.S. government has certain rights in the invention.

FIELD OF THE INVENTION

The present invention is directed to compositions and methods for preparing silk-based ionomeric compositions. These silk ionomeric compositions can be in a fluid state or a colloid state; can reversibly transform from one state to the other state in response to environmental stimuli such as pH; and are suitable for many applications, such as drug delivery, tissue engineering, sensor development, organic diodes, or absorbent materials.

BACKGROUND OF THE INVENTION

Silk-fibroin based biomaterials have been utilized for applications in biomedical and biotechnological fields. Several techniques for processing silk-fibroin have been developed, such as electrospinning, sonication, and chemical modification. Often, these processes yield silk biomaterials that are formed and/or stabilized through β-sheet assembly, with the size and distribution of the crystalline β-sheet regions regulating the mechanical properties and degradation rates of the silk biomaterials. See Jin H. J. et al., 3 Biomacromolecules 1233 (2002); Wang X. et al., 29 Biomaterials 1054 (2008); Murphy A. R. et al., 29 Biomaterials 2829 (2008); and Wang Y. et al., 29 Biomaterials 3415 (2008). Nevertheless, there remains a need for silk-based materials that present different characteristics, based on different mechanisms that can be used for various applications in the biomedical arena.

SUMMARY OF THE INVENTION

The present invention provides for compositions and methods for silk-based ionomeric compositions. Particularly, the present invention provides for silk-based ionomeric fluid suspensions (or particulate solutions) and colloids comprising ionomeric particles that are reversibly cross-linked through electrostatic interactions. The silk fibroin-based charged components of the ionomers can be obtained by covalently coupling silk fibroin molecules with poly amino acids (e.g., carbodiimide-mediated coupling reaction with poly-lysine hydrobromide (+) and poly-glutamic acid (−) sodium salts). The silk fibroin-based ionomer fluid suspensions and colloids can then be obtained by mixing the positively charged silk fibroins and negatively charged silk fibroins at neutral pH. The assembly of the ionomeric particles is driven by electrostatic interactions (i.e., acid-base reactions), and hence is pH-dependent and reversible. The silk-based ionomeric particles can exist in fluid suspensions (or particulate solutions) or colloids, depending on the concentration of the silk fibroin. The ionomeric particles can have a hydrophilic core formed by oppositely charged poly-amino acid chains associated through electrostatic interactions, and hydrophilic regions formed by silk fibroin backbones surrounding the hydrophobic core. The silk-based ionomeric particles are cyto-compatible (i.e., compatible with living cells), and can include active agents. For example, doxorubicin, a hydrophilic anti-tumor drug, can be loaded in the silk-based ionomeric composition to provide for control-release in a pH-dependent manner.

Accordingly, in one aspect, the present invention relates to a pH-dependent ionomeric composition comprising positive-charged silk fibroins and negative-charged silk fibroins. In certain embodiments, the pH-dependent ionomeric composition comprises silk fibroins with positively charged amino acid groups and silk fibroins with negatively charged amino acid groups. The composition forms ionomeric particles at neutral pH, in which the particles dissociate at acidic pH or basic pH. In some embodiments, the ionomeric particles can remain in a particulate solution at low fibroin concentration, e.g., at a fibroin concentration of about 1% to about 10% w/v. In some embodiments, the ionomeric particles can form a colloid at high fibroin concentrations, e.g., at a fibroin concentration of about 20% to about 30% w/v.

The silk fibroin-based ionomeric compositions of the present invention are capable of being reversibly transformed from charged fibroins to ionomeric particles, and of being reversibly transformed from charged fibroin to ionomeric particulate solutions or colloids, depending on environmental stimuli. These compositions are suitable for preparation into various materials and devices, such as an absorbent material, a contrast agent, a tissue implant, a sensor device, a biodelivery system, or a pharmaceutical formulation. Moreover, one or more active agents can be embedded in the silk fibroin ionomeric particles for various applications.

In another aspect, the present invention provides for a silk fibroin ionomeric colloid comprising positively charged silk fibroins and negatively charged silk fibroins, wherein at neutral pH the positively charged silk fibroins and the negatively charged silk fibroins form ionomeric particles that associate in a three-dimensional gel matrix via electrostatic interactions. The silk fibroin ionomeric colloid can be used in various applications, e.g., an absorbent material, a contrast agent, a diode, a tissue implant, a sensor device, and a biodelivery system.

In yet another aspect, the present invention provides for a pharmaceutical formulation comprising the pH-dependent ionomeric composition or silk fibroin ionomeric colloid, and a pharmaceutically acceptable excipient. In some embodiments, the pH-dependent ionomeric composition or silk fibroin ionomeric colloid can comprise at least one active agent.

Methods of preparing a silk fibroin ionomeric composition are also provided herein. The method includes providing positively charged silk fibroins; providing negatively charged silk fibroins; and mixing the positively and negatively charged silk fibroins at neutral pH to form a silk fibroin ionomeric particles or particle clusters associated via electrostatic interactions.

A further aspect of the present invention provides for a method of preparing an active agent-embedded silk fibroin ionomeric composition. The method includes providing a positively charged silk fibroin; providing a negatively charged silk fibroin; introducing at least one active agent to at least one of the charged silk fibroins; and mixing the charged fibroins and agent at neutral pH to form silk fibroin ionomeric particles or particle clusters associated via electrostatic interactions; wherein the active agent is embedded in the ionomeric particles or particle clusters. In one embodiment, the active agent is encapsulated inside the ionomeric particles. The method can then further include transforming the ionomeric particles to dissociated charged fibroins to release the at least one encapsulated active agent.

In yet another aspect, the present invention relates to a process of making a silk fibroin ionomeric particle composition. The process includes enriching silk fibroin functional groups to react with charged polymeric amino acids; reacting a first portion of the enriched silk fibroin with positively charged polymeric amino acids to form positively charged silk fibroins; reacting a second portion of the enriched silk fibroin with negatively charged polymeric amino acids to form negatively charged silk fibroins; and mixing the positively and negatively charged silk fibroins. At neutral pH, the charged fibroins reversibly form ionomeric particles or particle clusters via electrostatic interactions. At acidic or basic pHs, the charged fibroins remain disassociated.

The embodiments of the present invention also encompass the reversible silk fibroin-based ionomeric colloids or ionomeric particulate solutions, optionally including an active agent, that are prepared by methods described in different aspects of the present invention.

BRIEF DESCRIPTION OF THE DRAWINGS

FIG. 2A is a scheme showing the synthesis of the carboxy-silk fibroin intermediates. FIG. 2B presents the $^1$H-NMR spectral regions illustrating the conversion of silk fibroin to azo-silk fibroin and then to carboxy-silk fibroin.

FIG. 3A is a scheme showing the synthesis of silk fibroin-poly-lysine hydrobromide and silk fibroin-poly-glutamic acid sodium salt. FIG. 3B presents the $^1$H-NMR spectral regions illustrating the successful coupling of carboxy-silk fibroin with poly-lysine hydrobromide (PL) and with poly-glutamic acid sodium salt (PG), respectively.

DETAILED DESCRIPTION OF THE INVENTION

Figure 1:
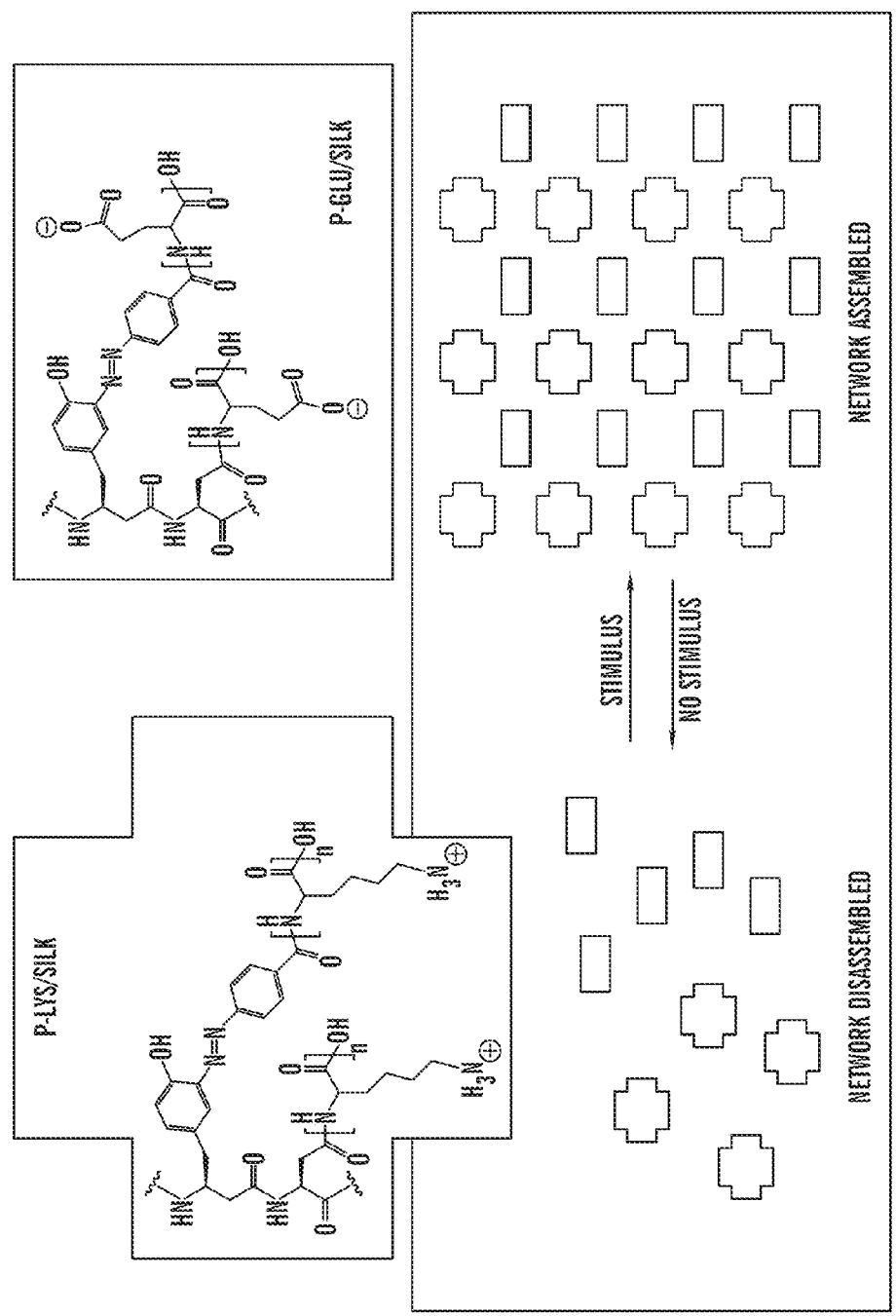
FIG. 1 is a schematic illustrating a concept of the association of the silk fibroin-poly-amino acid charged fibroins into ionomeric particles.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Embodiments of the present invention provide silk-based ionomeric compositions and colloids, pharmaceutical compositions comprising silk-based ionomeric colloids, and methods of making and applications thereof, such as an absorbent material, a contrast agent, a diode, a tissue implant, a sensor device and a biodelivery system. In accordance with the invention, the ionomeric composition is pH-dependent, and comprises positive-charged silk fibroins (e.g, silk-fiborin-poly-lysine hydrobromide) and negative-charged silk fibroins (e.g., silk-fibroin-poly-glutamic acid sodium salt). In such embodiments, the composition comprises silk fibroin ionomeric particles at neutral pH.

Silks have been employed for applications in biomedical and biotechnological fields. See Hofmann et al., 111 J Control Release 219 (2006); Lawrence et al., 30 Biomaterials 1299 (2009); Soffer et al., 19 Biomater Sci Polym Ed 653 (2008); and Sofia et al., 54 J. Biomed. Mater. Res. 139-48 (2001). Silk is popular because of its availability, the ease of purification (Sofia et al., 54 J. Biomed. Mater. Res. 139-48 (2001); Sohn et al., 5 Biomacromol. 751-57 (2004); and Um et al., 29 Int. J. Biol. Macromol. 91-97 (2001)), and its attractive properties. See Kaplan et al., in ACS Symposium Series, Vol. 544, 2-16 (McGrath & Kaplan, eds., Birkhauser, Boston, Mass., 1994); Kaplan et al., Protein Based Mats. 103-31 (McGrath & Kaplan, eds., Birkhauser, Boston, Mass., 1998); and Wang et al., 27 Biomats. 6064-82 (2006).

Silk has an unusual amino acid sequence: the bulk of the silk fibroin protein is organized into hydrophobic domains that are rich of alanine and glycine residues, and amino acids with large side chains that are clustered in chain-end hydrophilic blocks. See Bini et al., 335 J. Mol. Biol. 27-40 (2004). Structurally, the hydrophobic blocks assemble into crystalline regions while the hydrophilic blocks form less ordered regions. Zhou et al., 44 Proteins: Struct. Funct. Bioinf. 119-22 (2001). The large hydrophobic regions of silk fibroin are capable of assembling into crystalline β-sheet structures via intra- and inter-molecular hydrogen bonding and hydrophobic interactions, thus conferring unique features to the silk fibroin protein.

As used herein, the term "silk fibroin" includes silkworm fibroin and other insect or spider silk protein. Lucas et al., 13 Adv. Protein Chem. 107-242 (1958). Silk fibroin can be obtained from a solution containing a dissolved silkworm silk or spider silk. The silkworm silk fibroins are obtained, for example, from the cocoon of *Bombyx mori*, and the spider silk fibroins are obtained, for example, from *Nephila clavipes*. In the alternative, the silk fibroins suitable for use in the present invention can be obtained from a solution containing a genetically engineered silk harvested from bacteria, yeast, mammalian cells, transgenic animals or transgenic plants. See, e.g., WO 97/08315; U.S. Pat. No. 5,245,012.

Silk fibroin matrix can be prepared from an aqueous silk fibroin solution, which can be prepared from the silkworm cocoons using techniques known in the art. See, e.g., U.S. patent application Ser. No. 11/247,358; WO/2005/012606; WO/2008/127401. The silk aqueous solution can then be processed into silk fibroin matrices. Several processing techniques for preparing silk fibroin matrix have been reported, such as electrospinning (Jin et al., 3 Biomacromol. 1233-39 (2002)), sonication (Wang et al., 29 Biomats. 1054-64 (2008)) or chemical modification through covalent binding (Murphy et al., 29 Biomats. 2829-38 (2008)). These processes yield silk biomaterials that are formed and/or stabilized through β-sheet assembly, with the mechanical properties and enzymatic degradation rates of silks depending on the size and distribution of these crystalline β-sheet regions. See, e.g., Asakura et al., 42 Magn. Reson. Chem. 258-66 (2004). Such fibroin matrices can be used in conjunction with the silk fibroin-based ionomers of the present invention.

The present invention provides for silk fibroin-based ionomer compositions formed and/or stabilized through electrostatic interactions rather than β-sheet assembly. The association and dissociation of this silk fibroin-based ionomer composition can respond to stimuli, such as pH, temperature, ionic strength, electricity and/or shear stress variations (Shi & Berkland, 18 Adv. Mat. 2315-19 (2006); Wang et al., 20 Adv. Mat. 236-39 (2008)), e.g., as shown in FIG. 1. Such a versatile silk material can be suitable for many applications, such as drug delivery, tissue engineering, sensor development, organic diodes or absorbent materials.

Accordingly, in one aspect, the present invention relates to a pH-sensitive ionomeric composition comprising positively charged silk fibroins and negatively charged silk fibroins. The positively charged silk fibroins and negatively charged silk fibroins can form ionomeric particles or particle clusters at neutral pH, i.e., a pH close to 7.0 at 25° C. (77° F.) as measured by a pH meter. Because neutral pH can be affected by ionic concentration, (e.g., the pH of a 0.05 M potassium hydrogen phthalate solution can vary by as much as 0.5 pH units as a function of added potassium chloride), even though the added salt is neither acidic nor basic, "neutral pH" as used herein can range from pH6 to about pH8, or from about pH 6.5 to about pH 7.5, inclusive. In some embodiments, at least a collection of ionomeric particles or particle clusters can remain as charged silk fibroins (or dissociate from particle form) at acidic pH or basic pH. As used herein, "acidic pH" refers to a pH value below the neutral pH as defined herein, while "basic pH" refers to a pH value above the neutral pH as defined herein.

At about neutral pH and at low fibroin concentration, e.g., at a fibroin concentration of about 1% w/v to about 10% w/v, the silk ionomeric particles can remain in particulate solution (or fluid suspension). At about neutral pH and at high fibroin concentrations, e.g., at a fibroin concentration about 20% to about 30% w/v, the silk ionomeric particles can form a colloid. There may not be a clear phase difference between the "particulate solution" (i.e., suspension of particles in solution) and the "colloid", and these terms as used herein refer to the concentration difference of the silk fibroin ionomeric particles. The fibroin concentration can be infinitely low or infinitely high depending on the solubility of the individual charged silk fibroins.

In another aspect, the present invention relates to silk fibroin ionomeric colloids comprising positively charged silk fibroins and negatively charged silk fibroins, wherein at neutral pH the positively charged silk fibroins and the negatively charged silk fibroins form ionomeric particles that associate in a three-dimensional gel matrix via electrostatic interactions. These colloids can include an active agent, such as a drug or biologic.

The present invention also provides for methods of preparing a silk fibroin-based ionomeric composition. The method comprises the steps of providing positively charged silk fibroins; providing negatively charged silk fibroins; and mixing the positively and negatively charged silk fibroins. When the oppositely charged silk fibroins are mixed at about neutral pH, ionomeric particles or particle clusters are be formed via electrostatic interactions. These particles can include an active agent, such as a drug or biologic.

The terms "ionomeric composition", "silk ionomeric polymer", "silk-based ionomer", and "silk fibroin-based ionomer", as described herein, refer to silk fibroin-based polymers that comprise silk fibroins or modified silk fibroins containing ionic groups, that form the ionomeric polymer by ionic bonding (or electrostatic interaction) of these charged groups. The charged groups can bear one or more positive charges or negative charges. In some embodiments, the ionomeric composition or silk ionomeric polymer can be positively charged, negatively charged, or electrically neutral. A matrix of these ionomers contain microphase-separated ionic domains formed as a result of association or aggregation of these ionic groups. The ionomeric compositions of the invention comprise ionomeric particles formed by positively charged silk fibroin molecules and negatively charged silk fibroin molecules via electrostatic interaction.

In one embodiment, an ionomeric polymer can be produced by partially or fully neutralizing an acid group of silk fibroin molecules with a basic group of silk fibroin molecules. This network assembly of the ionomeric particles is reversible: responding to environmental stimuli, such pH change.

Silk fibroin-based charged components of the ionomeric composition of the invention can be prepared by reacting silk fibroin protein with a polar or ionic compound, or a salt thereof. In some embodiments, the polar or ionic group in the charged silk fibroin can be provided by a polar or charged polymer, or a salt thereof. In one embodiment, the polar or charged polymer is poly-amino acid, or a salt thereof. The poly-amino acid can be derived from natural amino acid or synthetic amino acids, or derivatives thereof. In one embodiment, a positively charged polymeric amino acid, or a salt thereof is used to prepare a positively charged silk fibroin. Exemplary positively charged polymeric amino acids include, but are not limited to, polylysine, polyarginine, polyhistidine, polyornithine, and combinations thereof. In one embodiment, a negatively charged polymeric amino acid, or a salt thereof is used to prepare a negatively charged silk fibroin. Exemplary negatively charged polymeric amino acids include, but are not limited to, polyglutamate, polyaspartate, and amides thereof as well as combinations thereof. In various embodiments, any positively charged polymers known to a skilled artisan (e.g., polyethylenimines and derivatives thereof, and carbohydrate polymer) and any negatively charged polymers known in the art (e.g., salt of polyacrylic acid, dextran sulfate and heparin) can also be used for the purpose of the invention. In some embodiments, acidic or basic polymers or polyamino acids can be used to prepare silk fibroin-based charged components of the ionomeric composition. It should be understood to a skilled artisan that, in at least some cases, the terms "acidic polyamino acid" and "negatively charged polyamino acid" are used interchangeably in the art. Similarly, basic polyamino acid can be referred as positively charged polyamino acids in the art.

Silk fibroin protein used to prepare charged silk fibroins can be modified or unmodified. Modification of silk fibroin protein, e.g., chemical modification of silk fibroin protein by enriching carboxyl groups in the protein, can increase the reactivity of silk fibroin protein with the desired polar or ionic compounds or polymers. In one embodiment, modification of silk fibroin protein can increase the charge density on the silk fibroin protein.

One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. patent application Ser. No. 11/407,373), diazonium coupling reaction (see, e.g., U.S. patent application Ser. No. 12/192,588), and pegylation with a chemically active or activated derivatives of the PEG polymer (see, e.g., PCT/US09/64673). Silk fibroin can also be modified through gene modification to alter functionalities of the silk protein (see, e.g., U.S. application Ser. No. 61/224,618). In some embodiments, the silk fibroins can be modified by one or more methods described herein.

The amino acids in the silk fibroin protein offer few alternatives for chemical functionalization. Silk fibroin derived from a *B. mori* silkworm is a fibrous protein (~420 kDa) composed of a heavy chain and a light chain that are linked together through a single disulfide bond. See Zhou et al., 44 Proteins 119 (2001); Tanaka et al., 1432 Biochim. Biophys. Acta 92-103 (1999). The majority of amino acids from the backbone of the silk fibroin are chemically inert, and the most attractive targets for chemical functionalization are the sparsely located amino acids containing carboxyl side chains. The original carboxyl content of silk fibroin protein, provided by the glutamic (E) and aspartic acid (D) residues, account for about 1.4% of the protein molecule.

In one embodiment, carboxyl content of the silk fibroin is enriched to increase the reactivity of silk fibroin protein with poly-amino acids, e.g., to achieve a high charge density on the resulting silk fibroin-poly-amino acid based ionomers. To enrich carboxyl content of silk fibroin, backbone amino acids suitable for chemical modification were altered. The most abundant amino acids that can be modified to carboxyl groups are tyrosine (Y) residues, which account for 5.2% of the total amino acids in the silk fibroin protein, and serine (S) residues that represent 11.9% of the protein. See Zhou et al., 44 Proteins 119 (2001); Asakura et al., 42 Magn Reson Chem 258 (2004). Theoretically, successful chemical modification of tyrosine (Y) and Serine (S) yields a total carboxyl content of 18.5% per silk fibroin molecule.

Figure 2A:
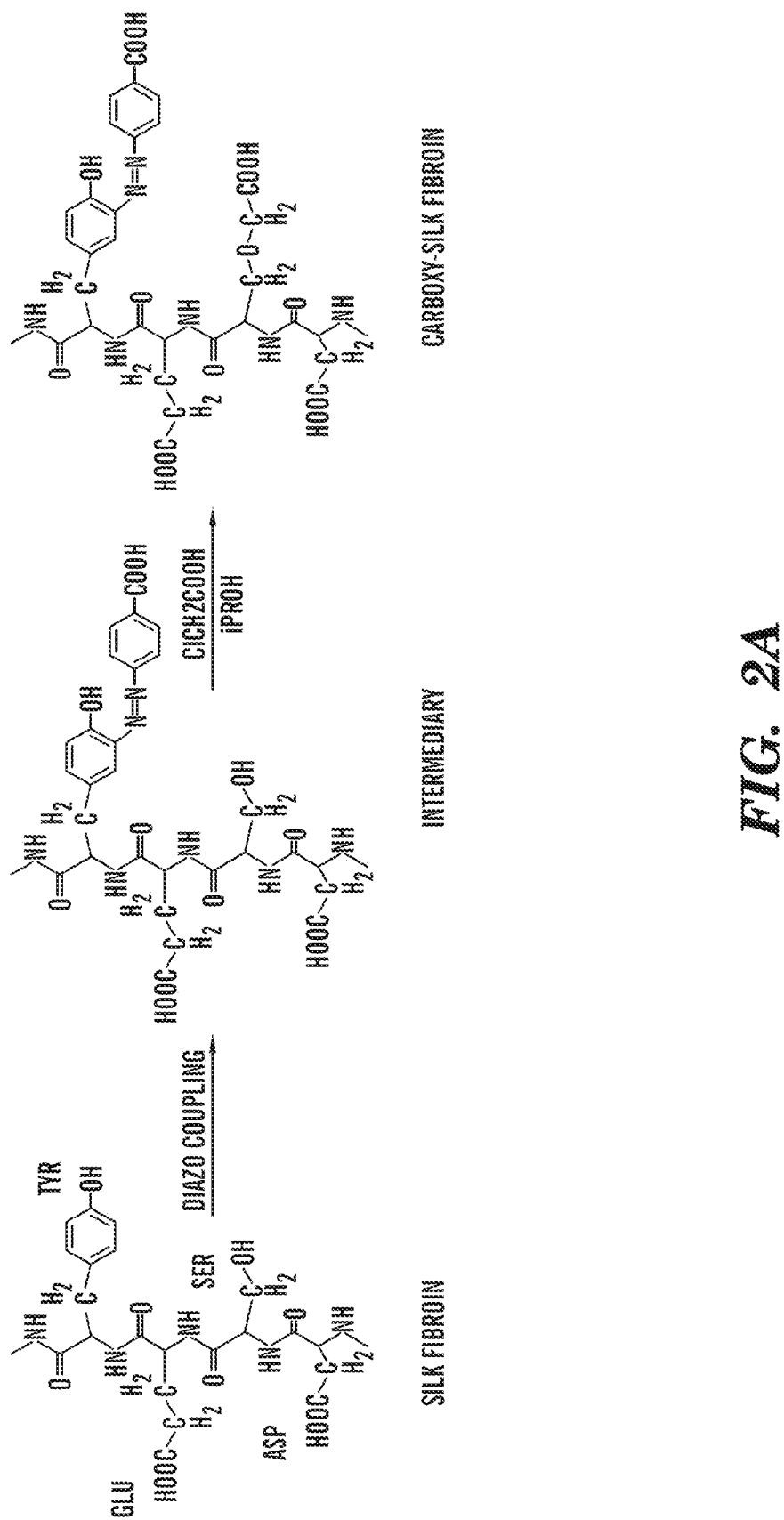
FIGS. 2A and 2B show synthesis and characterization of carboxy-silk fibroin.
Figure 2B:
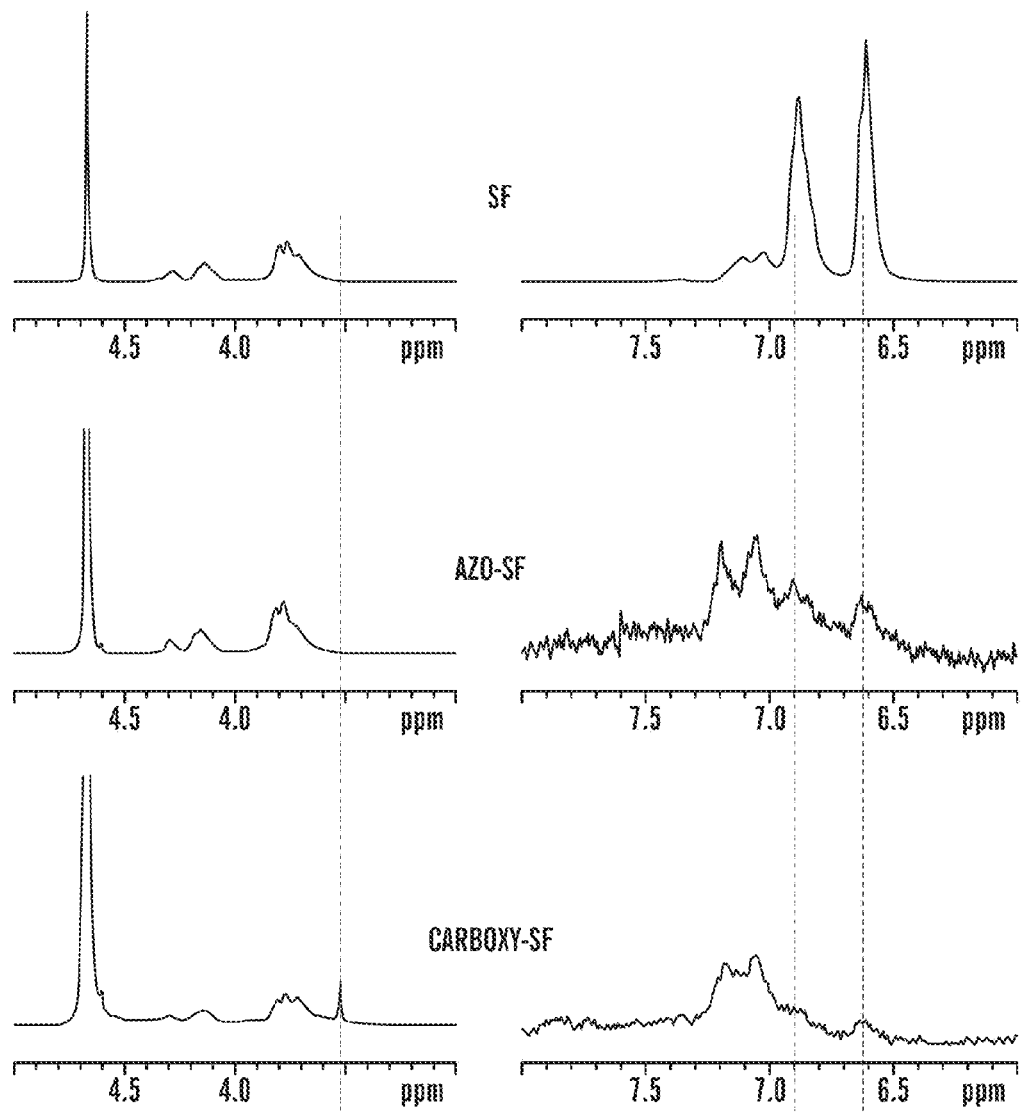

Accordingly, in one embodiment, tyrosine (Y) residues of degummed silk fibroins were coupled with a carboxyl-containing diazonium salt under alkaline conditions, yielding a yellow-orange azo-benzene-silk fibroin derivative ("azo-SF"); and serine (S) residues of azo-SF were reacted with chloroacetic acid under strong alkaline conditions to yield a carboxy-silk fibroin ("carboxy-SF") intermediate (FIG. 2A). The syntheses of the reaction intermediates, the azo-SF and carboxy-SF, were monitored by 1H-NMR. As shown in FIG. 2B, the azo-SF had new proton signals in the aromatic region of the spectrum (7.05 ppm to 7.19 ppm), corresponding to the additional benzene rings introduced by the diazonium coupling reaction; and the carboxy-SF intermediate had a new peak appearing at 3.52 ppm, corresponding to the methylene protons from the chloroacetic acid reactant.

In some embodiments, silk fibroin can be genetically engineered to be enriched in carboxyl content.

Reacting of silk fibroin protein with a polar or ionic compound (e.g., polymer or polyamino acid), or a salt thereof can be achieved by similar methods as those used for modification of silk fibroin proteins, as described herein, e.g., carbodiimide coupling reactions, diazonium coupling reactions, or charge-charge interactions. In some embodiments, other coupling methods known in the art can be used to link at least one polar or ionic compound (e.g., polymer or polyamino acid), or a salt thereof to the silk fibroin protein. A skilled artisan can determine appropriate protein-protein coupling methods (e.g., glutaraldehyde method) or protein-small coupling methods (e.g., mixed anhydride method) to prepare charged silk fibroins, e.g., based on the proteins and/or molecules to be coupled.

Figure 3A:
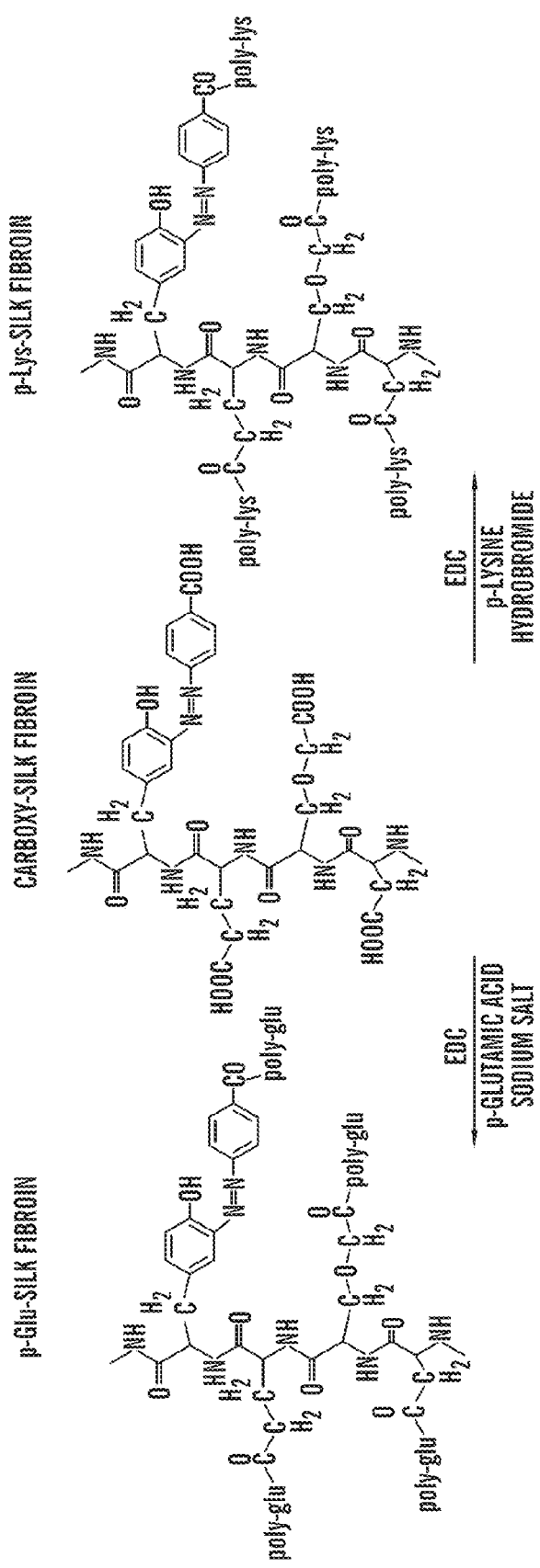
FIGS. 3A and 3B show synthesis and characterization of positively and negatively charged silk-based ionomers.
Figure 3B:
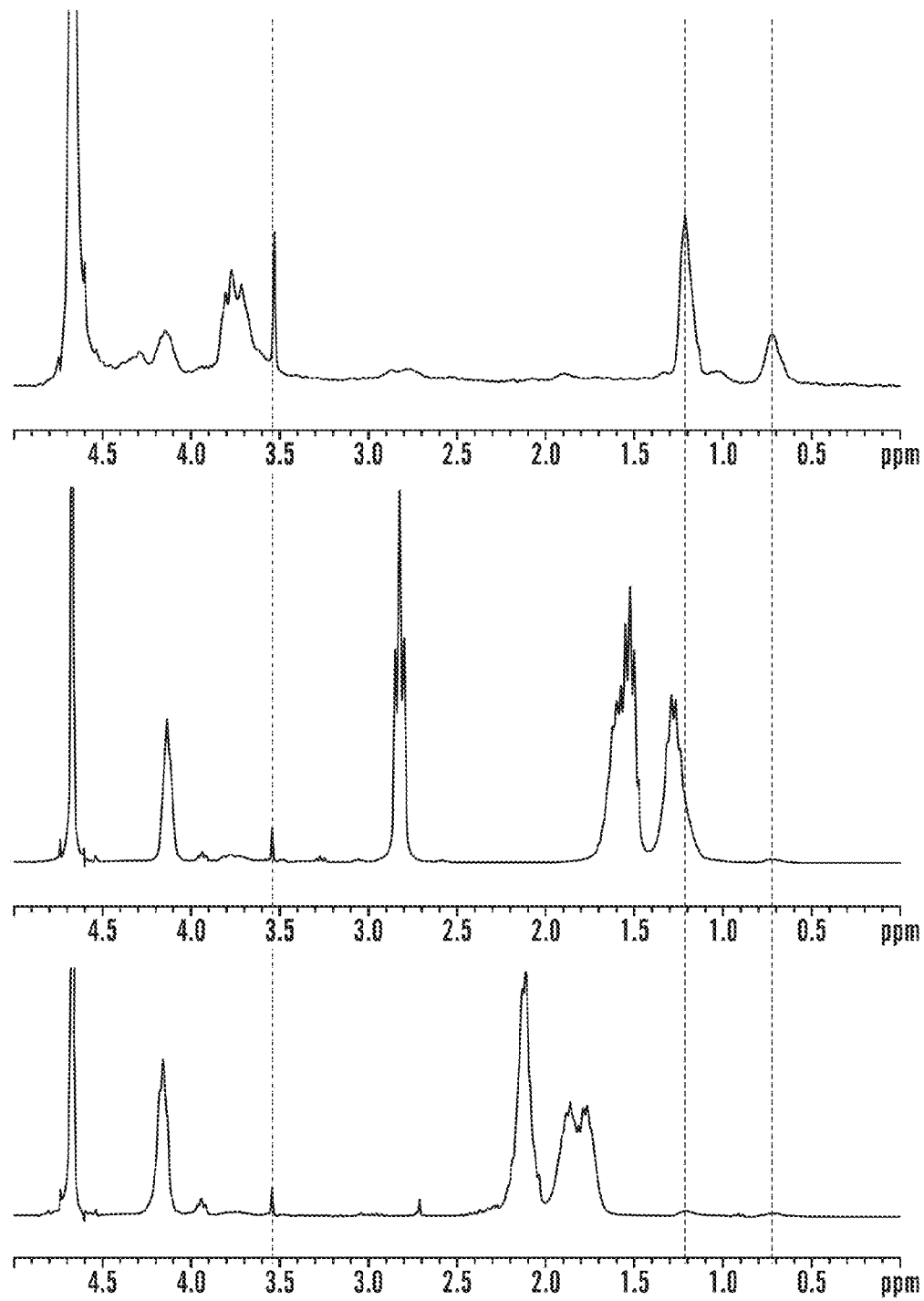

In one embodiment, charged polymeric natural amino acids with high molecular weight were attached to silk fibroin proteins to form charged silk fibroins. The positively and negatively charged silk fibroins were obtained by carbodiimide-mediated coupling reaction with either a polylysine hydrobromide (PL) or a poly-glutamic acid sodium salt (PG), respectively. The reaction schemes are shown in FIG. 3A. The structures of the two reaction products were confirmed by 1H-NMR. After coupling silk fibroin proteins with poly-amino acids, characteristic signals corresponding to the PL and PG in the 1.2 ppm to 4.2 ppm region of the spectra were observed, as shown in FIG. 3B. Passing these two reaction products through gel filtration columns did not change the $^1$H-NMR spectra, indicating that the poly-amino acids were covalently attached to the silk fibroin proteins.

Accordingly, some embodiments of the present invention provide a process of making a silk fibroin ionomeric particle composition. The process comprises the steps of modifying silk fibroin to enrich silk fibroin functional groups to react with charged polymeric amino acids; reacting a first portion of the modified silk fibroin with positively charged polymeric amino acids to form positive-charged silk fibroins; reacting a second portion of the modified silk fibroin with negatively charged polymeric amino acids to form negative-charged silk fibroins; and mixing the positive- and negative-charged silk fibroins at about neutral pH to form ionomeric particles or particle clusters via electrostatic interactions.

As described above, at high fibroin concentration, mixing of oppositely charged silk fibroins at about neutral pH, yields a silk ionomeric colloid (gel-like material, as particles incorporate water), comprising ionomeric particles or particles clusters. At low fibroin concentration, mixing of oppositely charged silk fibroin solutions at about neutral pH yields a particulate suspension of ionomer particles in solution. Diluting the silk ionomeric colloid formed at high fibroin concentration can also gradually change the ionomeric colloid to ionomeric particles suspended in solution. In other embodiments, at least one ionomeric particle or particle clusters can form at acidic pH or basic pH.

Figure 4:
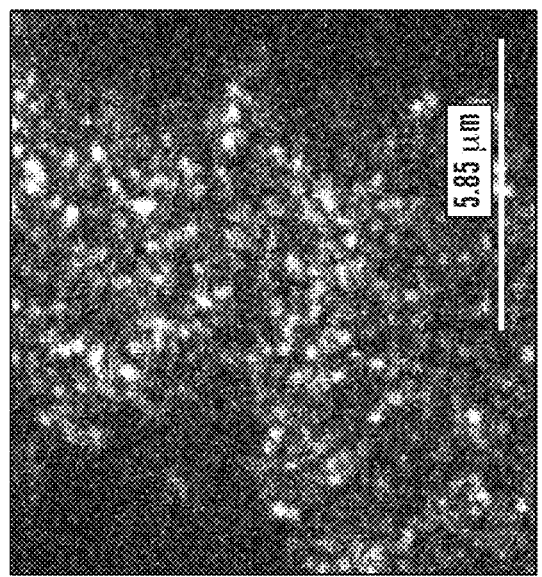
FIG. 4 is a set of images showing the confocal microscopic analysis of the colloidal gels formed at pH 7.0. The left panel shows the three-dimensional image of the particle distribution in the gel; and the right panel shows the two-dimensional image of the gel. The dimensions of the axes in the x, y, and z directions are 7 μm.
Figure 4:
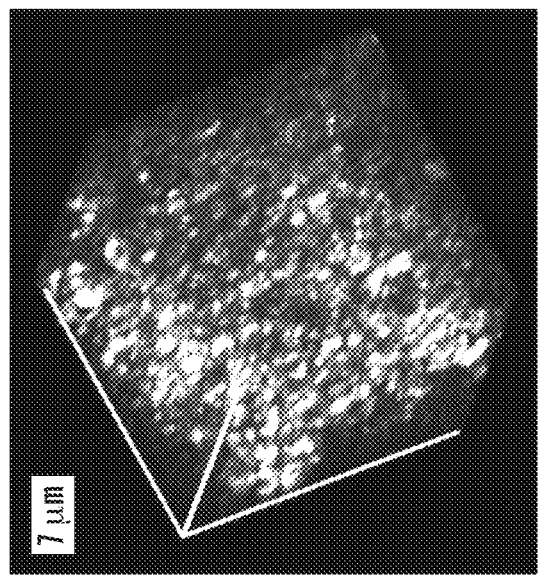
Figure 5:
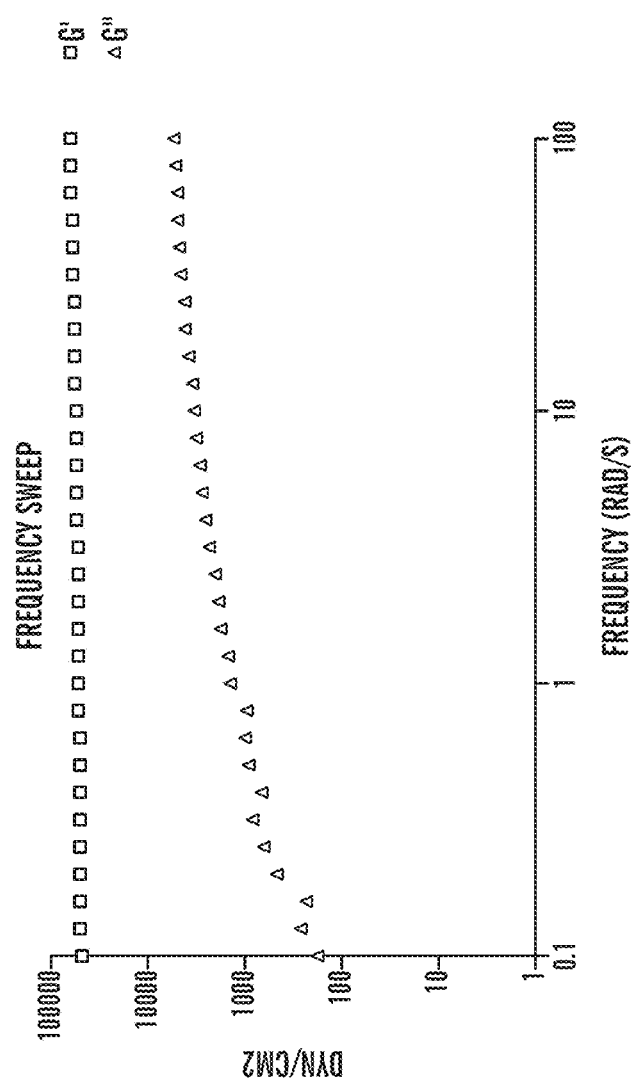
FIG. 5 is a graph presenting the results of dynamic oscillatory rheology measurement of one or more embodiments of the silk fibroin ionomeric colloid. The silk fibroin ionomeric colloid was obtained from mixing equal volumes of 25% w/v silk fibroin-PL and 25% w/v silk fibroin-PG solutions at pH 7. Shear storage modulus, G', is greater than the shear loss modulus, G", for the measured frequencies, indicating that the silk fibroin ionomeric colloid behaved as a gel. The frequency dependence of the shear modulus may due to the particulate nature of the colloid.

In one embodiment, the positive-charged and negative-charged silk fibroins can be mixed together to assess the networking properties of the charged silk fibroins at various pHs. For example, solutions of the silk fibroin-polylysine hydrobromide (silk fibroin-PL) and silk fibroin poly-glutamic acid sodium salt (silk fibroin-PG), e.g., each having a concentration of 25% w/v in water, can be prepared at different pH values ranging from 4.0 to 9.0. Equal volumes of the silk fibroin-PL and silk fibroin-PG having at the same pH value are then mixed together. The assembly of the oppositely charged silk fibroins under different pH values can be assessed using any method known in the art, e.g., viscosity measurement method, an imaging method, or a test tube inversion method. In one embodiment, the assembly of the oppositely charged silk fibroins is assessed by a test tube inversion method. The flow (solution) to no flow (gel or colloid) transition of the material can be monitored: a gel (or colloid) is considered formed when there was no observation of material fluidity or liquid accumulation on the bottom of the inverted vial/tube. The individual silk fibroin-poly amino acid solutions can form a yellow-orange, clear appearance. Upon mixing equal volumes of oppositely charged silk fibroin-poly amino acid solutions (i.e., silk fibroin-PL and silk fibroin-PG) at pH ~7.0, formation of gel-like colloidal composition can be observed, e.g., in FIG. 4. In some embodiments, formation of particulate suspension can be observed, depending on the concentrations of the charged silk fibroins. At pH ~6.0 and ~8.0, colloidal compositions can be formed within seconds, within minutes, or within hours, depending on the mixing condition, e.g., temperatures and charge density on silk fibroins. The composition formed at these pHs can appear not to incorporate as much water as in the composition formed at about neutral pH, hence resulting in a small amount of liquid accumulation outside the gel. Under more acidic (e.g., pH 4.0) or basic (e.g., pH 9.0) conditions, the assembly of the ionomers can be more impaired or cannot occur at all. Blending each of the charged silk fibroin solutions with the pure silk fibroin solution control (e.g., mixing silk fibroin-PL with pure silk fibroin solution such as uncharged silk fibroin solution, and mixing silk fibroin-PG with the pure silk fibroin solution such as uncharged silk fiborin solution, respectively) do not yield a colloidal composition, regardless of pH; nor do mixing the oppositely charged poly-amino acids (e.g., mixing PL with PG) without covalent bonding to silk fibroin yield an ionomeric composition.

As illustrated in FIG. 1, the association and dissociation of the silk fibroin-based ionomeric particles of the present invention is reversible in responsive to environmental stimuli. Hence, the fibroin ionomers can be reversibly transformed back to a dissociated charged silk fibroin solutions by adjusting a stimulus or stimuli. Accordingly, the colloid-to-solution (dissociated charged silk fibroin) state transition, or vice versa, of the silk fibroin-based ionomer composition can be controlled by at least one stimulus, for instance, changing pH of the composition, changing the ionic strength of the composition, changing the temperature of the composition, applying electricity or varying electric current to the composition, or applying or varying mechanical stress (e.g., shear stress, pressure) to the composition, or any combination thereof. In a particular embodiment, pH variance is used as an environmental stimulus. To evaluate the properties and/or responses of silk ionomeric compositions formed by oppositely charged silk fibroin-poly-amino acids mixed at pH ~7 to a pH change, small amounts of acid (e.g., 1N HCl) or base (1M NaOH) can be added to the formed silk gels. In such embodiments, the silk compositions can transition from a gel-like colloid state back to a solution state. In some embodiments, the silk compositions can transition to an intermediate state between a gel-like colloid state and a solution state. Depending on the pH values, various states of the silk ionomeric compositions can be formed as described herein. In another embodiment, the reversed transition (i.e. from a solution state to a gel-like colloid-state) can also be possible, e.g., by increasing or decreasing the pH value. For example, the silk solution formed by opposite-charged silk fibroin-poly-amino acids mixed at acidic or basic pH can transition from a solution state to a gel-like colloid upon neutralization of the mixture of the oppositely charged silk fibroin solutions, e.g., adjusting the pH of the mixture to about neutral pH.

Silk fibroin ionomeric compositions described herein typically comprise particles distributed three-dimensionally in the solution (low fibroin concentration) or colloid (high fibroin concentration). The sizes of the particles can range from 50 nm to 500 nm, inclusive. For instance, the particle sizes can range from about 100 nm to about 500 nm or from about 200 nm to about 400 nm, inclusive. It will be understood by one of ordinary skill in the art that particles usually exhibit a distribution of particle sizes around the indicated "size." In one embodiment, the term "size" as used herein refers to the mode of a size distribution of particles, i.e., the value that occurs most frequently in the size distribution. In another embodiment, the term "size" as used herein refers to the average of a size distribution of particles. Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light, confocal or electron microscopy).

Figure 6:
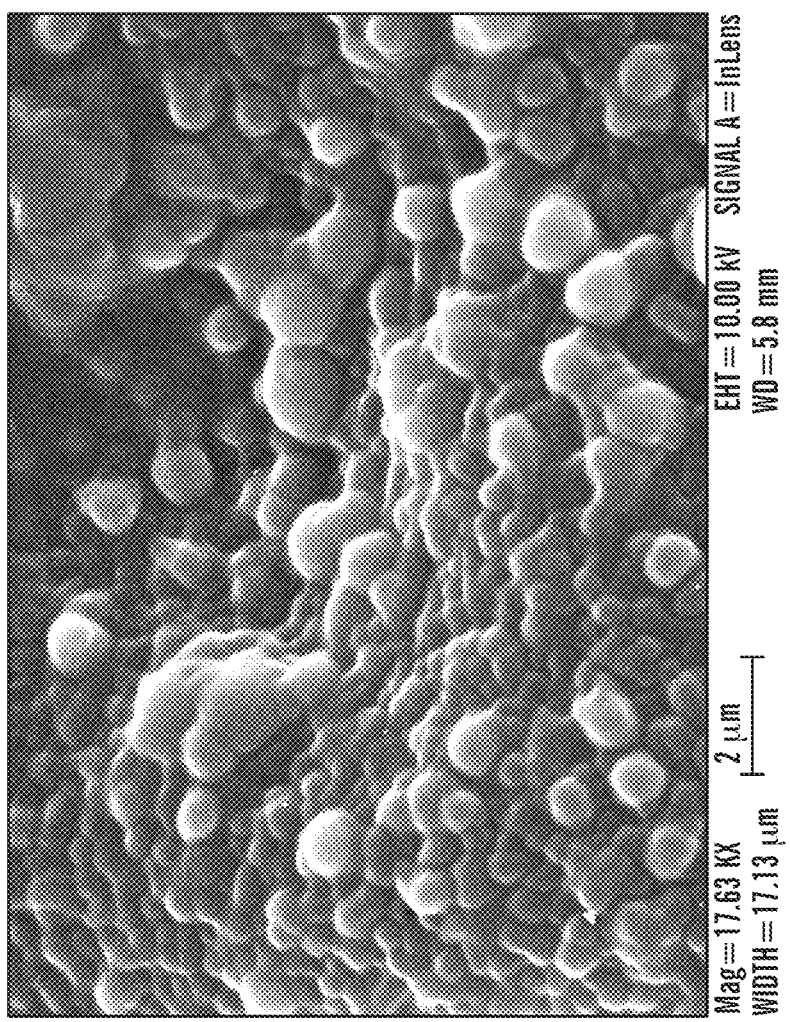
FIG. 6 is a scanning electron micrograph (SEM) of one or more embodiments of the silk fibroin ionomeric compositions described herein. The SEM shows the presence of particles with different sizes in the colloids. The samples were prepared by mixing 5% w/v silk fibroin-PL and 5% w/v silk fibroin-PG solutions. For imaging purpose, the composition samples were dried overnight and coated with Pt/Pd.

In one embodiment, the detailed structure of an embodiment of a silk fibroin-based colloid is characterized by confocal imaging. For example, FIG. 4B shows that high magnification confocal imaging confirms the presence of three-dimensionally distributed particles in the silk ionomeric composition. In one embodiment, the size of the particles can be calculated by measuring the width of the half-maximum pixel intensity of individual features. One embodiment of the silk fibroin-based ionomeric particles has an average radius of 247±33 nm. The shape and size of the particles formed can be investigated further by scanning electron microscopy (SEM) and dynamic light scattering (DLS). For example, SEM images obtained from nickel-spattered samples can confirm the presence of spherical particles of various sizes (FIG. 6). DLS measurements can indicate slightly larger sizes of the particles (ranging from about 337 nm to 399 nm) compared with the confocal measurements. One of skill in the art can vary the size of silk-based ionomeric particles, e.g., by altering charge density on the silk fibroins, the charged polymer or polyamino acid coupled to the silk fibroins, and/or environmental stimuli. In some embodiments, a time-dependent increase of the particle size in solution can be observed, which can indicate the swelling of particles due to water uptake of particles in solutions as demonstrated in Table 1.

TABLE 1

Change of particle size with increased residence time of particles in solution (ultrapure water) measured by DLS

|   | Time in solution (min) | Diameter (nm) |
|---|---|---|
| 1 | 20 | 399 |
| 2 | 25 | 482 |
| 3 | 30 | 625 |

The silk fibroin-based ionomeric compositions or colloids of the present invention can also include at least one active agent. Forming the ionomeric compositions or colloids that comprise at least one active agent can be achieved by introducing the active agent to at least one of the charged silk fibroin solutions prior to mixing the charged silk fibroin solutions. Alternatively, the active agent can be introduced to the silk fibroin-based ionomeric composition or colloid during or after mixing the charged silk fibroin solutions. Additionally, the active agent can be introduced to the ionomeric composition or colloid before, during, or after the formation of an ionomeric or particle suspension or colloid (e.g., after pH is adjusted). In various embodiments, the active agent can be distributed in the ionomeric compositions or colloids, e.g., inside ionomeric particles. In some embodiments, the active agent can be distributed on the surface of ionomeric particles.

The variety of active agents that can be used in conjunction with the silk fibroin-based ionomer composition of the present invention is vast. For example, the active agent can be a therapeutic agent or biological material, such as cells, proteins, peptides, nucleic acid analogues, nucleotides, oligonucleotides, nucleic acids (DNA, RNA, siRNA), peptide nucleic acids, aptamers, antibodies or fragments or portions thereof, antigens or epitopes, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, chemotherapeutic agents, small molecules, drugs (e.g., drugs, dyes, amino acids, vitamins, antioxidants) and combinations thereof.

Exemplary antibiotics suitable for inclusion in the silk ionomer composition of the present invention include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, or fusidic acid.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

Exemplary antibodies include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, and laccase.

Additional active agents to be used herein include cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R. G. Landes Co., Austin, Tex., 1995); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, and steroids.

In some embodiments, the active agent can also be an organism such as a bacterium, fungus, plant or animal, or a virus. Moreover, the active agent can include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents can also include therapeutic compounds, such as pharmacological materials, vitamins, sedatives, hypnotics, prostaglandins and radiopharmaceuticals.

Accordingly, some embodiments of the present invention provide for a method of preparing an active agent-embedded silk fibroin ionomer composition. The method comprises the steps of providing a positively charged silk fibroin; providing a negatively charged silk fibroin; introducing at least one active agent to at least one of the charged silk fibroins; and mixing the charged silk fibroins at about neutral pH to form ionomeric particles or particle clusters associated via electrostatic interactions, wherein the active agent is embedded in the ionomeric particles or particle clusters.

Figure 7:
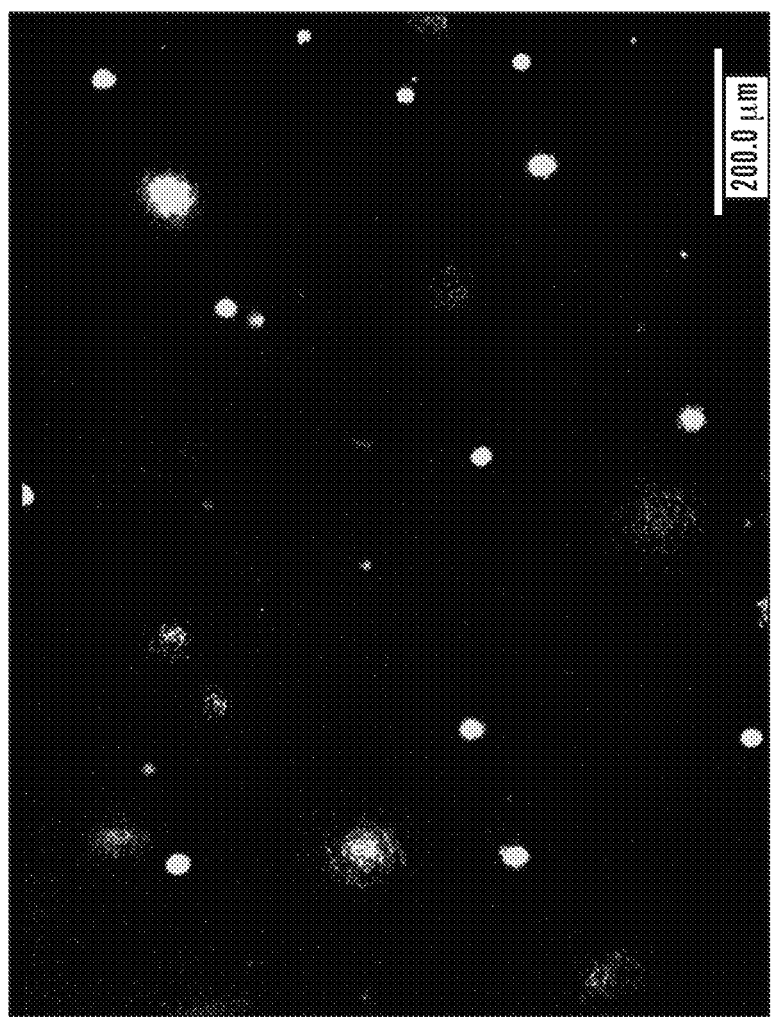
FIG. 7 is an image demonstrating the cytocompatibility of one embodiment of the silk fibroin ionomeric compositions described herein. The image is an overlay of live cells and dead cells. Images were taken after 72 hours of cell incubation in the silk fibroin ionomeric composition. The bright dots indicate live cells.

In an aspect of the present invention, the silk fibroin-based ionomers are cytocompatible, i.e. compatible with biological materials, e.g., cells. The cytocompatibility of the silk fibroin-based ionomeric colloidal compositions can be assessed by any methods known to a skilled artisan, e.g., performing a live/dead cell assay using the desired cell lines or lineages, e.g., primary human cervical fibroblasts. For example, equal volumes of silk fibroin-PL solution and silk fibroin-PG solution at pH ~7.0 can be mixed at high fibroin concentration in the presence of cells to achieve an in situ gelation and cell entrapment. After 72 hours of incubation, the cells can be stained to assess the viability. In some embodiments, the cell viability in the colloidal compositions can be estimated to be at least about 40%, at least about 50%, at least about 60%, or at least about 70%. In one embodiment, the cell viability in the colloidal compositions is estimated to be in the range of about 80% to 90% range. For example, as shown in FIG. 7, the fluorescent images indicate that cells can be well distributed in the colloidal composition, and have a rounded morphology. Without wishing to be bound by theory, the morphological outcome can be caused by the lack of cell adhesion and attachment sites in the colloidal composition, as the poly-amino acid side chains in the colloidal composition can be likely oriented towards the inside of the silk fibroin-based ionomeric particles. In some embodiments, the silk-fibroin based compositions can sustain cell viability, but they may not favor cell attachment or spreading. In some embodiments, the silk-fibroin based compositions can sustain cell viability and allow cell attachment or spreading. In such embodiments, the cell attachment or spreading in the silk-fibroin based compositions can be enhanced, e.g., by mixing extracellular matrix molecules (such as fibronectin, collagen, gelatin) with the charged silk-fiborin proteins before or during the formation of ionomeric compositions or colloids.

Characterizations of the particulate nature of the silk fibroin-based ionomeric compositions by confocal imaging, SEM and DLS in conjunction with the characterization of the morphology of the cells in situ entrapped in the compositions appeared to indicate that the assembly of the silk fibroin-based ionomers occurred via differential orientation of the hydrophobic and hydrophilic parts of the molecules. Although not being bound by theory, it appears that an assembly model of the silk fibroin-based ionomers can be established: particles can be formed by association of oppositely charged silk fibroins; and the particles have hydrophilic cores composed of network of oppositely charged poly-amino acid side chains associated through electrostatic interactions and hydrophobic regions formed by silk fibroin backbones surrounding the hydrophilic cores. This assembly model may help explain the lack of cell attachment and spreading when cells are encapsulated in the silk ionomeric compositions; and it may also rationalize the increase of particle sizes as the water uptake into the hydrophilic core of the particles. In some embodiments, the ionomeric particles of the invention are partially water-soluble or water-insoluble.

The capability of silk ionomer composition to transform reversibly from ionomeric particles to dissociated charged fibroins (e.g., from colloid to fluid at high fibroin concentration, or from particle suspension to fluid at low fibroin concentration), and vice versa, confers additional benefits to silk ionomer composition of the present invention. For example, silk ionomer composition can be used to make biodelivery system and pharmaceutical formulation. Controlled release of at least one bioactive agent from the silk ionomer composition can be achieved by controlling the association and dissociation of the silk ionomer network through applying different stimuli. Controlled release of the active agent permits active agent to be released sustainably over time, with controlled release kinetics. In some instances, a bioactive agent can be delivered continuously to the site where treatment is needed, for example, over several weeks or several months, therefore obtaining preferred treatments. The controlled delivery vehicle is advantageous because it protects the bioactive agent from degradation in vivo in body fluids and tissue, for example, by proteases.

The active agent can be encapsulated within the core of the ionomeric particles, depending on the sizes of the active agent and the particles and the hydropathy of the active agent. In one embodiment, the active agent is hydrophilic and hence can be encapsulated in the hydrophilic core of the particles. Encapsulating active agent in the core of the particles can further prolong the release time and provide further protection for the active agent. In alternative embodiments, the active agent is hydrophobic, and hence can be distributed in the core or on the surface of the ionomeric particles, depending on the hydrophobicity of the particle cores.

In one embodiment, the silk fibroin ionomeric composition is a colloid, the active agent can be encapsulated within the ionomer particles or can be disposed in the interstitial space between the particles. Applying stimuli to the colloid can transform the colloid to fluid, releasing active agent either encapsulated within particles or disposed in the interstitial space.

In one embodiment, a bioactive agent can be embedded in a biodelivery device comprising silk ionomer particles; silk ionomeric particles can transport the bioactive agent to a target site without affecting non-target sites (e.g., may be implanted at a particular site within an animal or human); and when appropriate environmental stimulus is present, such as the variance of pH or electric potential, the particles or particle clusters can disintegrate or dissociate and release the bioactive agent (e.g., over time). For example, the intratumoral environment is generally acidic or hypoxic. The ionomeric particles comprising at least one anti-tumor agent distributed therein can disintegrate or dissociate and release the therapeutic agent when they reach the tumor. Accordingly, the ionomeric particles comprising at least one therapeutic agent described herein can be used as a therapeutic drug carrier for treatment of diseases, e.g., cancer. In one embodiment, the ionomeric particles comprising at least one therapeutic agent can be used for targeted drug delivery.

Controlled release from the silk ionomeric composition or colloid can be designed to occur over a pre-defined period of time, for example, for greater than about 12 hours or 24 hours, greater than one month or two months or five months. The time of release can be selected, for example, to occur over a time period of about 12 hours to 24 hours, or about 12 hours to 1 week. In another embodiment, release can occur, for example, on the order of about 1 month to 2 months, about 1 month to 3 months, or about 1 month to 6 months. The controlled release time can be selected based on the condition treated. For example, slow release can be more effective for wound healing or chemotherapy wherein consistent release and high local dosage are desired. The release profile of an active agent, e.g., a therapeutic agent, from the silk ionomeric composition can be modified by a number of factors, e.g., concentrations of charged silk fibroins, charge density on the silk fibroins, drug to be released from the composition, and/or charged polymers or poly-amino acids coupled to the silk fibroins to make charged silk fibroins. Thus, one of skill in the art can optimize the release profile of the active agent accordingly.

In one embodiment, a pharmaceutical formulation can be prepared comprising the silk fibroin-based ionomer composition having embedded active or bioactive agent(s). The formulation can be administered to a patient in need of the particular bioactive agent that has been embedded in the fibroin-based ionomer composition.

The pharmaceutical formulation can be administered by a variety of routes known in the art including topical, oral, ocular, nasal, transdermal or parenteral (including intravenous, intraperitoneal, intramuscular and subcutaneous injection as well as intranasal or inhalation administration) and implantation. The delivery can be systemic, regional, or local. Additionally, the delivery may be intrathecal, e.g., for drug delivery to central nervous system.

In addition to the silk ionomer composition, the pharmaceutical formulation can also contain a targeting ligand. Targeting ligand refers to any material or substance which can promote targeting of the pharmaceutical formulation to tissues and/or receptors in vivo and/or in vitro with the formulations of the present invention. The targeting ligand can be synthetic, semi-synthetic, or naturally-occurring. Materials or substances which can serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin.

The pharmaceutical formulations can also encompass precursor targeting ligands. A precursor to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and iodo acetyl groups.

The pharmaceutical formulations can contain common components found in other pharmaceutical formulations, such as known pharmaceutically acceptable excipients. As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Exemplary excipients include diluents, solvents, buffers, or other liquid vehicle, solubilizers, dispersing or suspending agents, isotonic agents, viscosity controlling agents, binders, lubricants, surfactants, preservatives, stabilizers and the like, as suited to particular dosage form desired. The formulations can also include bulking agents, chelating agents, and antioxidants. Where parenteral formulations are used, the formulation can additionally or alternately include sugars, amino acids, or electrolytes.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; oils such as peanut oil, cottonseed oil; safflower oil, sesame oil; olive oil; corn oil and soybean oil; esters such as ethyl oleate and ethyl laurate; agar; non-toxic compatible lubricants such as sodium lauryl sulfate and magnesium stearate; polyols, for example, of a molecular weight less than about 70,000 kD, such as trehalose, mannitol, and polyethylene glycol. See, e.g., U.S. Pat. No. 5,589,167. Exemplary surfactants include nonionic surfactants, such as Tween surfactants, polysorbates, such as polysorbate 20 or 80, etc., and the poloxamers, such as poloxamer 184 or 188, pluronic polyols, and other ethylene/polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc. Coloring agents, releasing agents, coating agents, sweetening, flavoring and perfuming agents, preservatives and antioxidants can also be present in the composition, according to the judgment of the formulator.

The pharmaceutical formulations containing the therapeutic agent (active agent or bioactive agent)-embedded silk ionomer composition can be administered in a controlled-release manner, similarly as described above, so that portions of the therapeutic agent can be released in a subject over a period of time. As used herein, a "subject" can mean a human or an animal. Examples of subjects include, but are not limited to, primates (e.g., humans, and monkeys) and rodents (e.g., mice and rats). In one embodiment, the subject is a mammal. The mammal can be a human, non-human primate, mouse, rat, dog, cat, horse, or cow, but are not limited to these examples. In addition, the pharmaceutical formulations described herein can be employed in domesticated animals and/or pets.

In one embodiment, the pharmaceutical formulation can be administered so that the therapeutic agent is slowly and gradually released in the patient from the silk ionomer composition over a period of time. For instance, less than about 5%, about 10%, about 15%, about 20%, about 25%, or about 30%, inclusive, of the therapeutic agent is released in the patient from the silk ionomer composition in ten days, and the rest of the therapeutic agent is gradually release over a period of more than 1 month, 2 months, 3 months, 5 months or 6 months, inclusive.

When administering the bioactive agent in a controlled-release manner, the bioactive agent remains active in the silk ionomer composition so that it can perform its function upon release. Generally, the activity of the bioactive agent in the silk ionomer composition remains at a significant quantity that can sustain bioactive effects within a relevant period of time, which can be a week, a month, or even a year.

In one embodiment, the loading and releasing of a drug, e.g., doxorubicin, in the silk fibroin ionomeric particle composition can be assessed to test the applicability of the compositions as drug delivery systems. Such drug delivery tests can also further confirm the assembly model of the silk fibroin-based ionomers, as described above. Doxorubicin is a fluorescent, hydrophilic chemotherapeutic agent. Without being bound by theory, it appears that if the assembly of particles occurs via the aforementioned model, doxorubicin can then be entrapped in the hydrophilic core of particles and slowly released from the particles. In the other embodiments, if the particle cores are hydrophobic, the drug would then have been nonspecifically bound to the surface of particles and would have been released in "burst" mode.

Figure 8:
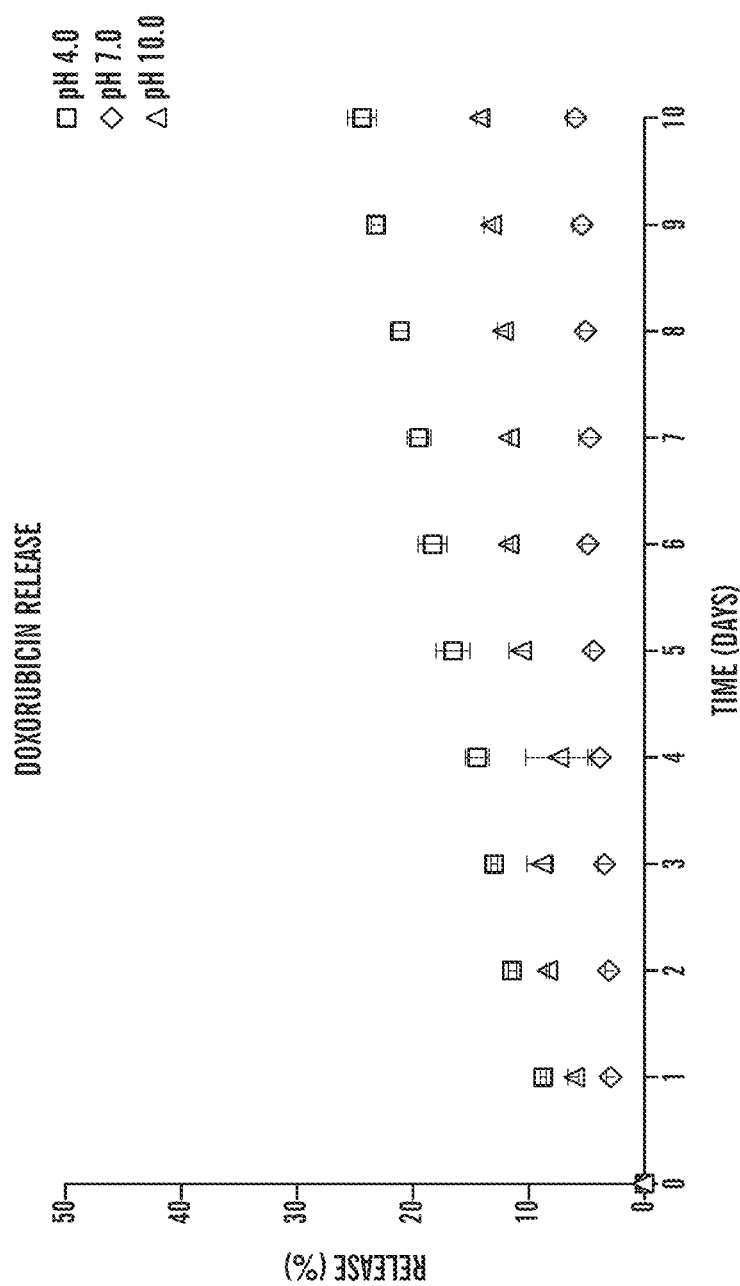
FIG. 8 is a graph showing the pH-dependent release profile of doxorubicin from one embodiment of the silk fibroin-based ionomeric particles prepared according to aspects of the present invention.

In one embodiment, drug-loaded ionomeric particles can be formed at about neutral pH, e.g., in the presence of the drug such as doxorubicin. The drug-loaded particles can be prepared by dissolving silk fibroin-PL and silk fibroin-PG in a desired concentration of the drug, e.g., 250 µg/ml doxorubicin solutions, in buffered solutions, e.g., 1×PBS, each at about neutral pH (e.g., pH ~7.4); and then mixing the resulting solutions, e.g., in about equal volumes. In some embodiments, the loading capacity achieved can be approximately 4 µg drug per mg of particles (i.e., ~100 µg doxorubicin can be loaded per 0.5 ml of 5% w/v particles). The drug release profile for drug loaded particles at three different pH values can be monitored daily over a pre-defined period of time, e.g., a 10-day period or longer. In some embodiments, the drug-loaded ionomeric particles can have a drug release profile of about at least 0.001 µg drug/mg particle/day, or at least about 0.01 µg drug/mg particle/day, at about neutral pH. In some embodiments, the drug-loaded ionomeric particles can have a drug release profile of about at least 0.01 µg drug/mg particle/day, or at least about 0.05 µg drug/mg particle/day, at about acidic or basic pHs. In one embodiment, as shown in FIG. 8, at pH ~7.0, about 6% of the loaded drug, e.g., doxorubicin, can be released over ~10 days, corresponding to a release rate of ~0.024 µg drug/mg particles/day; and at basic or acidic pHs, about 15% (pH ~10.0) and about 25% (pH ~4.0) of the drug, e.g., doxorubicin, can be released, corresponding to release rates of ~0.06 µg drug/mg particle/day (pH 10.0); and 0.1 µg drug/mg particle/day (pH 4.0), respectively. These data indicated that the loaded drug can be entirely released from the drug loaded silk composition in about 167 days at pH ~7.0; about 67 days at pH ~10.0; and about 40 days at pH ~4.0.

The pH-dependent drug release profile of drug loaded silk fibroin-based compositions can be useful for cancer therapy and can circumvent many classical chemotherapy issues. See Bidros & Vogelbaum, 6 Neurotherapeutics 539-46 (2009); Lee et al., 132 J. Contr. Release 164-70 (2008). For example, doxorubicin is typically administered as a single intravenous injection (40 mg/m$^2$ to 60 mg/m$^2$) every 21 to 28 days to minimize side effects. It was suggested that extracellular pH values of solid tumor are in the range of pH 5.7 to pH 7.8. See van Sluis et al., 41 Magn. Reson. Med. 743-50 (1999). Injection of drug-loaded silk ionomer-based particles into the tumor could lead to enhanced permeability and retention, and can provide consistent, localized and control-released drug dosage. Moreover, the differential drug release rate of drug-loaded silk ionomer-based particles can locally deliver a high enough drug dose to target malignant cells, and hence decrease the cytotoxic effect on normal tissues.

The use of silk-based materials in the form of nano- and microspheres has been reported previously, with particle sizes ranging between 35 nm to 440 µm and drug release time ranging between 8 hours to 4 weeks. See Gupta et al., 4 Int. J. Nanomed. 115-22 (2009); Wang et al., 117 J. Control. Release 360-70 (2007); Wang et al., 134 J. Control. Release, 81-90 (2009); Wenk et al., 132 J. Control. Release, 26-34 (2008); Wilz et al., 29 Biomats. 3609-16 (2008). These silk spheres were formed with β-sheet structures. The ionomeric particles of the present invention, however, are formed though a different stabilization mechanism that is driven by electrostatic interactions. Moreover, the observed drug release rates of the drug loaded silk ionomer-based particles (e.g., doxorubicin) are comparatively slower than those of the reported silk spheres, and hence can provide prolonged drug delivery.

The drug delivery systems or pharmaceutical formulations comprising silk fibroin-based ionomeric compositions of the invention can be used for prevention, diagnosis and/or treatment of different diseases.

In one embodiment, the silk-based ionomeric composition can be made as an eye gel, eye ointment, or eye drop to deliver eye medication used for diagnosis purpose, e.g., to dilate (enlarge) the pupils or to dye the ocular surface for eye examinations, or for treatment purpose, e.g., to treat dry eyes, eye allergies, eye infections, eye inflammation, such as conjunctivitis, blepharitis; amblyopia, strabismus, diabetic retinopathy, myopia, macular degeneration, ocular histoplasmosis and the like. The eye medication that can be embedded in the silk ionomeric composition include, but are not limited to artificial tears (to lubricate the eye) such as carboxymethyl cellulose, hydroxypropyl methylcellulose, and hydroxypropyl cellulose; antihistamines, such as diphenhydramine, doxylamine, loratadine, desloratadine, fexofenadine, pheniramine, cetirizine, promethazine, chlorpheniramine, levocetirizine, quetiapine, meclizine, and dimenhydrinate; ocular decongestants (to decrease redness) such as tetrahydrozoline, ephedrine, levo-methamphetamine, naphazoline, oxymetazoline, phenylephrine, phenylpropanolamine, propylhexedrine, pseudoephedrine, synephrine; and combinations thereof.

In one embodiment, the silk-based ionomeric composition can be made into a prosthesis or device to deliver active ingredient in the body in various application such as in orthopaedic applications such as bone filling materials, arthroplasty devices (e.g., hip and knee prostheses), orthopedic implants (e.g., hip, knee, shoulder and elbow prosthesis, bone cements, prosthetic joint components), maxillofacial implants and devices (e.g., skull, face, and jaw prostheses), dental applications such as dental filling materials, dental prosthetic devices (e.g., crowns, bridges, removable prostheses), dental implants (e.g. osseointegrated implant), and orthodontic appliances (e.g. dental retainer), maxillofacial implants and devices (e.g., skull, face, and jaw prostheses), spinal devices or implants (e.g., spinal cord, spinal column, spine cage) and osteosynthesis devices; devices and implants in traumatology application such as would healing devices or implants (skin, bone, and vascular wound grafts and patches, sutures, vascular wound repair devices, hemostatic dressings); cardiovascular devices and implants such as blood vessel prosthesis, stents, catheters, vascular grafts, heart valves and pacemakers; coagulation devices such as argon enhanced coagulation devices with coated probes; implantable artificial organs (e.g. artificial heart, liver, kidney, lungs, brain pacemaker and the like); and the like.

The silk fibroin-based ionomeric composition of the invention can be prepared to contain and release substantially any therapeutic agent. Examples of some pharmaceutics agents can include: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives e.g., aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents; angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors; $\beta_2$ agonists (e.g. salbutamol, terbutaline, clenbuterol, salmeterol, formoterol); steroids such glycocorticosteroids, preferably antiinflammatory drugs (e.g. Ciclesonide, Mometasone, Flunisolide, Triamcinolone, Beclomethasone, Budesonide, Fluticasone); anticholinergic drugs (e.g. ipratropium, tiotropium, oxitropium); leukotriene antagonists (e.g. zafirlukast, montelukast, pranlukast); xantines (e.g. aminophylline, theobromine, theophylline); Mast cell stabilizers (e.g. cromoglicate, nedocromil); inhibitors of leukotriene synthesis (e.g. azelastina, oxatomide ketotifen); mucolytics (e.g. N-acetylcysteine, carbocysteine); pain relievers in general such as analgesic and anti-inflammatory drugs, including steroids (e.g. hydrocortisone, cortisone acetate, prednisone, prednisolone, methylpredniso lone, dexamethasone, betamethasone, triamcino lone, beclometasone, fludrocortisone acetate, deoxycorticosterone acetate, aldosterone); and non-steroid antiinflammatory drugs (e.g. Salicylates such as aspirin, amoxiprin, benorilate, coline magnesium salicylate, diflunisal, faislamine, methyl salicylate, salicyl salicylate); Arylalkanoic acids such as diclofenac, aceclofenac, acematicin, etodolac, indometacin, ketorolac, nabumetone, sulindac tolmetin; 2-Arylpropionic acids (profens) such as ibuprofen, carprofen, fenbufen, fenoprofen, flurbiprofen, ketoprofen, loxoprofen, naproxen, tiaprofenic acid; N-arylanthranilic acids (fenamic acids) such as mefenamic acid, meclofenamic acid, tolfenamic acid; Pyrazolidine derivatives such as phenylbutazone, azapropazone, metamizole, oxyphenbutazone; Oxicams such as piroxicam, meloxicam, tenoxicam; Coxib such as celecoxib, etoricoxib, lumiracoxib, parecoxib, rofecoxib (withdrawn from market), valdecoxib (withdrawn from market); Sulphonanilides such as nimesulide; others such as licofelone, omega-3 fatty acids; cardiovascular drugs such as glycosides (e.g. strophantin, digoxin, digitoxin, proscillaridine A); respiratory drugs; antiasthma agents; bronchodilators (adrenergics: albuterol, bitolterol, epinephrine, fenoterol, formoterol, isoetharine, isoproterenol, metaproterenol, pirbuterol, procaterol, salmeterol, terbutaline); anticancer agents (e.g. cyclophosphamide, doxorubicine, vincristine, methotrexate); alkaloids (i.e. ergot alkaloids) or triptans such as sumatriptan, rizatriptan, naratriptan, zolmitriptan, eletriptan and almotriptan, than can be used against migraine; drugs (i.e. sulfonylurea) used against diabetes and related dysfunctions (e.g. metformin, chlorpropamide, glibenclamide, glicliazide, glimepiride, tolazamide, acarbose, pioglitazone, nateglinide, sitagliptin); sedative and hypnotic drugs (e.g. Barbiturates such as secobarbital, pentobarbital, amobarbital; uncategorized sedatives such as eszopiclone, ramelteon, methaqualone, ethchlorvynol, chloral hydrate, meprobamate, glutethimide, methyprylon); psychic energizers; appetite inhibitors (e.g. amphetamine); antiarthritis drugs (NSAIDs); antimalaria drugs (e.g. quinine, quinidine, mefloquine, halofantrine, primaquine, cloroquine, amodiaquine); antiepileptic drugs and anticonvulsant drugs such as Barbiturates, (e.g. Barbexaclone, Metharbital, Methylphenobarbital, Phenobarbital, Primidone), Succinimides (e.g. Ethosuximide, Mesuximide, Phensuximide), Benzodiazepines, Carboxamides (e.g. Carbamazepine, Oxcarbazepine, Rufinamide) Fatty acid derivatives (e.g. Valpromide, Valnoctamide); Carboxilyc acids (e.g. Valproic acid, Tiagabine); Gaba analogs (e.g. Gabapentin, Pregabalin, Progabide, Vigabatrin); Topiramate, Ureas (e.g. Phenacemide, Pheneturide), Carbamates (e.g. emylcamate Felbamate, Meprobamate); Pyrrolidines (e.g. Levetiracetam Nefiracetam, Seletracetam); Sulfa drugs (e.g. Acetazolamide, Ethoxzolamide, Sultiame, Zonisamide) Beclamide; Paraldehyde, Potassium bromide; antithrombotic drugs such as Vitamin K antagonist (e.g. Acenocoumarol, Dicumarol, Phenprocoumon, Phenindione, Warfarin); Platelet aggregation inhibitors (e.g. antithrombin III, Bemiparin, Deltaparin, Danaparoid, Enoxaparin, Heparin, Nadroparin, Pamaparin, Reviparin, Tinzaparin); Other platelet aggregation inhibitors (e.g. Abciximab, Acetylsalicylic acid, Aloxiprin, Ditazole, Clopidogrel, Dipyridamole, Epoprostenol, Eptifibatide, Indobufen, Prasugrel, Ticlopidine, Tirofiban, Treprostinil, Trifusal); Enzymes (e.g. Alteplase, Ancrod, Anistreplase, Fibrinolysin, Streptokinase, Tenecteplase, Urokinase); Direct thrombin inhibitors (e.g. Argatroban, Bivalirudin, Lepirudin, Melagatran, Ximelagratan); other antithrombotics (e.g. Dabigatran, Defibrotide, Dermatan sulfate, Fondaparinux, Rivaroxaban); antihypertensive drugs such as Diuretics (e.g. Bumetanide, Furosemide, Torsemide, Chlortalidone, Hydroclorothiazide, Chlorothiazide, Indapamide, metolaxone, Amiloride, Triamterene); Antiadrenergics (e.g. atenolol, metoprolol, oxprenolol, pindolol, propranolol, doxazosin, prazosin, teraxosin, labetalol); Calcium channel blockers (e.g. Amlodipine, felodipine, dsradipine, nifedipine, nimodipine, diltiazem, verapamil); Ace inhibitors (e.g. captopril, enalapril, fosinopril, lisinopril, perindopril, quinapril, ramipril, benzapril); Angiotensin II receptor antagonists (e.g. candesartan, irbesartan, losartan, telmisartan, valsartan); Aldosterone antagonist such as spironolactone; centrally acting adrenergic drugs (e.g. clonidine, guanabenz, methyldopa); antiarrhythmic drug of Class I that interfere with the sodium channel (e.g. quinidine, procainamide, disodyramide, lidocaine, mexiletine, tocamide, phenyloin, encamide, flecamide, moricizine, propafenone), Class II that are beta blockers (e.g. esmolol, propranolol, metoprolol); Class III that affect potassium efflux (e.g. amiodarone, azimilide, bretylium, clorilium, dofetilide, tedisamil, ibutilide, sematilide, sotalol); Class IV that affect the AV node (e.g. verapamil, diltiazem); Class V unknown mechanisms (e.g. adenoide, digoxin); antioxidant drugs such as Vitamin A, vitamin C, vitamin E, Coenzime Q10, melanonin, carotenoid terpenoids, non carotenoid terpenoids, flavonoid polyphenolic; antidepressants (e.g. mirtazapine, trazodone); antipsychotic drugs (e.g. fluphenazine, haloperidol, thiotixene, trifluoroperazine, loxapine, perphenazine, clozapine, quetiapine, risperidone, olanzapine); anxyolitics (Benzodiazepines such as diazepam, clonazepam, alprazolam, temazepam, chlordiazepoxide, flunitrazepam, lorazepam, clorazepam; Imidaxopyridines such as zolpidem, alpidem; Pyrazolopyrimidines such as zaleplon); antiemetic drugs such as Serotonine receptor antagonists (dolasetron, granisetron, ondansetron), dopamine antagonists (domperidone, droperidol, haloperidol, chlorpromazine, promethazine, metoclopramide) antihystamines (cyclizine, diphenydramine, dimenhydrinate, meclizine, promethazine, hydroxyzine); antiinfectives; antihystamines (e.g. mepyramine, antazoline, diphenihydramine, carbinoxamine, doxylamine, clemastine, dimethydrinate, cyclizine, chlorcyclizine, hydroxyzine, meclizine, promethazine, cyproheptadine, azatidine, ketotifen, acrivastina, loratadine, terfenadine, cetrizidinem, azelastine, levocabastine, olopatadine, levocetrizine, desloratadine, fexofenadine, cromoglicate nedocromil, thiperamide, impromidine); antifungus (e.g. Nystatin, amphotericin B., natamycin, rimocidin, filipin, pimaricin, miconazole, ketoconazole, clotrimazole, econazole, mebendazole, bifonazole, oxiconazole, sertaconazole, sulconazole, tiaconazole, fluconazole, itraconazole, posaconazole, voriconazole, terbinafine, amorolfine, butenafine, anidulafungin, caspofungin, flucytosine, griseofulvin, fluocinonide) and antiviral drugs such as Anti-herpesvirus agents (e.g. Aciclovir, Cidofovir, Docosanol, Famciclovir, Fomivirsen, Foscarnet, Ganciclovir, Idoxuridine, Penciclovir, Trifluridine, Tromantadine, Valaciclovir, Valganciclovir, Vidarabine); Anti-influenza agents (Amantadine, Oseltamivir, Peramivir, Rimantadine, Zanamivir); Antiretroviral drugs (abacavir, didanosine, emtricitabine, lamivudine, stavudine, tenofovir, zalcitabine, zidovudine, adeforvir, tenofovir, efavirenz, delavirdine, nevirapine, amprenavir, atazanavir, darunavir, fosamprenavir, indinavir, lopinavir, nelfinavir, ritonavir, saquinavir, tipranavir); other antiviral agents (Enfuvirtide, Fomivirsen, Imiquimod, Inosine, Interferon, Podophyllotoxin, Ribavirin, Viramidine); drugs against neurological dysfunctions such as Parkinson's disease (e.g. dopamine agonists, L-dopa, Carbidopa, benzerazide, bromocriptine, pergolide, pramipexole, ropinipole, apomorphine, lisuride); drugs for the treatment of alcoholism (e.g. antabuse, naltrexone, vivitrol), and other addiction forms; vasodilators for the treatment of erectile dysfunction (e.g. Sildenafil, vardenafil, tadalafil), muscle relaxants (e.g. benzodiazepines, methocarbamol, baclofen, carisoprodol, chlorzoxazone, cyclobenzaprine, dantrolene, metaxalone, orphenadrine, tizanidine); muscle contractors; opioids; stimulating drugs (e.g. amphetamine, cocaina, caffeine, nicotine); tranquillizers; antibiotics such as macrolides; aminoglycosides; fluoroquinolones and β-lactames; vaccines; cytokines; hormones including birth-control drugs; sympathomimetic drugs (e.g. amphetamine, benzylpiperazine, cathinone, chlorphentermine, clobenzolex, cocaine, cyclopentamine, ephedrine, fenfluramine, methylone, methylphenidate, Pemoline, phendimetrazine, phentermine, phenylephrine, propylhexedrine, pseudoephedrine, sibutramine, symephrine); diuretics; lipid regulator agents; antiandrogen agents (e.g. bicalutamide, cyproterone, flutamide, nilutamide); antiparasitics; blood thinners (e.g. warfarin); neoplastic drugs; antineoplastic drugs (e.g. chlorambucil, chloromethine, cyclophosphamide, melphalan, carmustine, fotemustine, lomustine, carboplatin, busulfan, dacarbazine, procarbazine, thioTEPA, uramustine, mechloretamine, methotrexate, cladribine, clofarabine, fludarabine, mercaptopurine, fluorouracil, vinblastine, vincristine, daunorubicin, epirubicin, bleomycin, hydroxyurea, alemtuzumar, cetuximab, aminolevulinic acid, altretamine, amsacrine, anagrelide, pentostatin, tretinoin); hypoglicaemics; nutritive and integrator agents.

In some embodiments, the cytocompatible silk fibroin-based ionomer compositions of the invention can be used to encapsulate cells for cell-based therapy. For example, stem cells can be encapsulated inside the silk fibroin-based ionomer compositions for stem cell-based therapy.

The silk fibroin-based ionomer compositions of the invention can be used readily in fabrication of sensor devices or phase-changed materials. Because of the capability of silk ionomer composition to reversibly transform between a colloid (or particle suspension) state and a fluid state, the composition of the invention can be used to sense environmental stimuli, such as changes in pH, ionic strength, current or electric potential, redox state, temperature, stress levels (e.g., stress stress levels or pressure levels), among other factors. The sensor devices of the present invention can be used readily in environmental and life sciences, where biocompatibility and biodegradability are paramount. For example, the sensor as described herein can be used to monitor a natural environment (e.g., in the human body) and may be implanted in vivo without a need to retrieve the device at a later time. Moreover, the sensor devices of the present invention can be dispersed in the environment, again without the need to retrieve them at a later time, thereby providing novel and useful devices for sensing and detection.

Tissue engineering scaffolds can be prepared from silk fibroin-based ionomer colloid. As described in some embodiments of the present invention, cell viability can be sustained in the silk ionomer colloidal composition. In some embodiments, little or no cell attachment or spreading can be observed. Hence, the silk ionomeric composition can be used as an tissue implant such as adhesion barrier material.

Moreover, the silk fibroin-based ionomer compositions can also be used to fabricate gel diode device. For example, silk fibroin-based colloid gel containing oppositely charged silk fibroin-poly-amino acid carrying counter ions can be sandwiched between electrodes and sealed by spacers (e.g., ion permeable membrane). Varying electric current on the ionomeric gels can result ion transport and electron conduction. The diode made from silk fibroin-based ionomer composition can be useful in semiconductor application, particularly in fabricating flexible, biocompatible and biodegradable electronic circuits. Such circuit can be an integration into implants in animal and human tissue and can perform various functions, such as sensing, interfacing, controlling functions for drug delivery, prosthetics, and neural-electronic integration. In some embodiments, the silk fibroin-based ionomer compositions can be included in organic batteries.

Additionally, the silk fibroin-based ionomeric composition of the invention can be used as absorbent materials, such as a liquid-absorbent material or a shock-absorbent material.

The silk-based ionomeric composition can have a wide range of concentration when used in different applications. The fibroin concentration in the colloid or particle suspension may not be limited by the original concentration of the silk fibroin solution, as modification of silk fibroin may increase the solubility of silk fibroin in solution. Hence, silk ionomer composition can be enriched in solution to a concentration higher than about 30% w/v or 40% w/v, depending on the solubility of charged silk fibroin. A high concentration of silk fibroin colloid can be desirable for moldable colloid used as, e.g., a moldable tissue implant. Lower concentrations of the silk fibroin ionomer composition can be achieved by mixing low concentrations of oppositely charged silk fibroin solutions or diluting the high-concentration silk ionomer composition to a diluted suspension of silk ionomeric particles. For example, depending on the anticipated applications, a diluted suspension of silk ionomer particles may be desired for drug delivery through injection.

The silk-based ionomer composition can also be used as a contrast agent. For example, heavy ions or ionic compound or polymers may be conjugated on the silk fibroin protein to form charged silk fibroins. Alternatively, heavy atoms or molecules can be embedded in the silk ionomeric compositions as contrast media. The silk ionomer composition can be administered as a fluid, particle suspension or as colloid, and when administered as fluid, can transform to a particle suspension or a colloid in response to a stimulus.

The silk-based ionomer compositions, when used in various applications, can be available as ready-to-use format, such as a fluid, a diluted suspension of particles, or a colloidal gel, depending on the desired application.

Alternatively, a kit comprising a pair of oppositely charged silk-based ionomers, each in a separately container, can be provided with an instruction carrying the methods of making ionomer composition and controlling the state of the ionomer composition, as described herein.

The present invention may be defined in any of the following numbered paragraphs:

1. A pH-dependent ionomeric composition comprising positive-charged silk fibroins and negative-charged silk fibroins; wherein at neutral pH the composition comprises silk fibroin ionomeric particles.
2. The pH-dependent ionomeric composition of paragraph 1, wherein the size of the ionomeric particles ranges from about 200 nm to about 500 nm, inclusive.
3. The pH-dependent ionomeric composition of paragraph 1 or 2, further comprising at least one active agent.
4. The pH-dependent ionomeric composition of any of the preceding paragraphs, wherein the positively charged silk fibroins comprise positively charged polymeric amino acids selected from the group consisting of polylysine, polyarginine, polyhistidine, and any combination thereof.
5. The pH-dependent ionomeric composition of any of the preceding paragraphs, wherein the negatively charged silk fibroins comprise negatively charged polymeric amino acids selected from the group consisting of polyglutamate, polyaspartate, and any combination thereof.
6. The pH-dependent ionomeric composition of any of the preceding paragraphs, wherein transformation from ionomeric particles to disassociated charged fibroins is reversibly controlled by changing at least one factor selected from the group consisting of pH, ionic strength, temperature, electrical charge, and shear stress.
7. A silk fibroin ionomeric colloid comprising positively charged silk fibroins and negatively charged silk fibroins, wherein at neutral pH the charged silk fibroins form ionomeric particles that associate in an ionomeric gel matrix via electrostatic interactions.
8. The silk fibroin ionomeric colloid of paragraph 7, further comprising at least one active agent.
9. The silk fibroin ionomeric colloid of paragraph 7 or 8, wherein the positively charged silk fibroins comprise positively charged polymeric amino acids selected from the group consisting of polylysine, polyarginine, polyhistidine, and any combination thereof.
10. The silk fibroin ionomeric colloid of any of paragraphs 7-9, wherein the negatively charged silk fibroins comprise negatively charged polymeric amino acids selected from the group consisting of polyglutamate, polyaspartate, and any combination thereof.
11. The silk fibroin ionomeric colloid of any of paragraphs 7-10, wherein the size of the ionomeric particles ranges from about 200 nm to about 500 nm, inclusive.
12. The silk fibroin ionomeric colloid of any of paragraphs 7-11, wherein transformation from colloid to disassociated charged fibroins is reversibly controlled by at least one of (a) changing pH of the colloidal gel; (b) changing the ionic strength of the colloid gel; (c) changing the temperature of the colloid gel; (d) applying electricity to the colloid gel; and (e) applying shear stress to the colloid gel.
13. An absorbent material comprising the pH-dependent ionomeric composition of any of paragraphs 1-6 or the silk fibroin ionomeric colloid of any of paragraphs 7-12.
14. A contrast agent comprising the pH-dependent ionomeric composition of any of paragraphs 1-6 or the silk fibroin ionomeric colloid of any of paragraphs 7-12.
15. A diode comprising the pH-dependent ionomeric composition of any of paragraphs 1-6 or the silk fibroin ionomeric colloid of any of paragraphs 7-12.
16. A tissue implant comprising the pH-dependent ionomeric composition of any of paragraphs 1-6 or the silk fibroin ionomeric colloid of any of paragraphs 7-12.
17. A sensor device comprising the pH-dependent ionomeric composition of any of paragraphs 1-6 or the silk fibroin ionomeric colloid of any of paragraphs 7-12.
18 A biodelivery system comprising the silk fibroin ionomeric colloid of any of paragraphs 7-12.
19. A pharmaceutical formulation comprising the silk fibroin ionomeric colloid of any of paragraphs 7-12, and a pharmaceutically acceptable excipient.
20. A biodelivery system comprising the pH-dependent ionomeric composition of any of paragraphs 1-6.
21. A pharmaceutical formulation comprising the pH-dependent ionomeric composition of any of paragraphs 1-6, and a pharmaceutically acceptable excipient.

22. A method of preparing a silk fibroin ionomeric composition, comprising the steps of:
providing positively charged silk fibroins;
providing negatively charged silk fibroins; and
mixing the positively and negatively charged silk fibroins at neutral pH to form silk fibroin ionomeric particles or particle clusters associated via electrostatic interactions.

23. An active agent-embedded silk fibroin ionomeric composition formed by steps comprising:
providing a positive-charged silk fibroin solution;
providing a negative-charged silk fibroin solution;
introducing at least one active agent to at least one of the charged silk fibroin solutions; and
mixing the charged silk fibroin solutions at neutral pH to form silk fibroin ionomeric particles or particle clusters, wherein the active agent is embedded in the ionomeric particles or particle clusters.

24. The active agent-embedded silk fibroin ionomeric composition of paragraph 23, wherein the active agent is encapsulated inside the ionomeric particles.

25. The active agent-embedded silk fibroin ionomeric composition of paragraph 23 or 24, further comprising the step of transforming from ionomeric particles to disassociated charged fibroins to release at least one active agent.

26. The active agent-embedded silk fibroin ionomeric composition of any of paragraphs 23-25, wherein the transforming is induced by adjusting at least one factor selected from the group consisting of pH, electricity, ionic strength, temperature, and shear stress.

27. The active agent-embedded silk fibroin ionomeric composition of any of paragraphs 23-26, wherein the active agent is selected from the group consisting of cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, and drugs.

28. The active agent-embedded silk fibroin ionomeric composition of any of paragraphs 23-27, wherein the active agent is hydrophilic.

29. The active agent-embedded silk fibroin ionomeric composition of any of paragraphs 23-28, wherein at acidic pH, the active agent is released from the composition for a period of about 1 month.

30. The active agent-embedded silk fibroin ionomeric composition of any of paragraphs 23-29, wherein at basic pH, the active agent is released from the composition for a period of about 2 months.

31. The active agent-embedded silk fibroin ionomeric composition of any of paragraphs 23-30, wherein at neutral pH, the active agent is released from the composition for a period of about 5 months.

32. A silk fibroin ionomeric particle composition made by the process of:
modifying silk fibroin to enrich fibroin functional groups to react with charged polymeric amino acids;
reacting a first portion of the modified silk fibroin with positively charged polymeric amino acids to form positively charged silk fibroins;
reacting a second portion of the modified silk fibroin with negatively charged polymeric amino acids to form negatively charged silk fibroins; and
mixing the positively and negatively charged silk fibroins at neutral pH to form ionomeric particles via electrostatic interactions.

33. The silk fibroin ionomeric particle composition of paragraph 32, wherein the modifying is selected from the group consisting of carbodiimide coupling reaction, diazonium coupling reaction, and charge-charge interaction.

34. The silk fibroin ionomeric particle composition of paragraph 32 or 33, wherein the reacting is selected from the group consisting of carbodiimide coupling reaction, diazonium coupling reaction, and charge-charge interaction.

35. The silk fibroin ionomeric particle composition of any of paragraphs 32-34, further comprising the step of introducing at least one active agent into the composition.

EXAMPLES

Example 1

Materials

Para-toluene sulfonic acid, 4-amino benzidine, sodium nitrate, chloroacetic acid, poly-lysine hydrobromide (MW 15,000 Da) and poly-glutamic acid sodium salt (MW 15,000 Da) were purchased from Sigma-Aldrich (St. Louis, Mo.). The zero-length crosslinker 1-ethyl-3-[3-dimethylaminopropyl]carbodiimide hydrochloride (EDC) was purchased from Thermo Fisher Scientific (Rockford, Ill.).

Silk fibroin solution was obtained as previously described. See Perry et al., 2008; McCarthy et al., 54 J. Biomed. Mats. Res. 139 (2001); Murphy et al., 29 Biomaterials 2829 (2008). Briefly, *Bombyx mori* cocoons were cleaned and cut into small pieces. In a subsequent degumming process, sericin, a water-soluble glycoprotein bound to raw silk fibroin filaments, was removed from the silk strands by boiling *Bombyx mori* cocoons in a 0.02 M aqueous solution of $NaCO_3$ for 60 min. The silk fibroin was then dissolved in a 9 M LiBr solution at 60° C. for 1 hr to generate a 20% (w/v) silk fibroin solution. The solution was dialyzed in Slide-A-Lyzer® 3.5K MWCO dialysis cassettes (Pierce Chemicals, Rockford, Ill.) against water for 72 hr to remove the LiBr.

The silk fibroin solution may be diluted to a lower concentration. Moreover, the silk fibroin solution may be concentrated, for example, to about 30% (w/v). See, e.g., WO 2005/012606. Briefly, the silk fibroin solution with a lower concentration may be dialyzed against a hygroscopic polymer, such as PEG, amylose or sericin, for a time period sufficient to result in a desired concentration.

Additionally, silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; U.S. application Ser. No. 61/227,254; Ser. No. 61/224,618; Ser. No. 12/192,588.

Regarding the synthesis of charged silk fibroins, polyamino acid coupled silk fibroin was obtained by enriching the carboxy content of the silk fibroin molecule, and then coupling poly-lysine hydrobromide and poly-glutamic acid sodium salt, respectively, to silk fibroin via carbodiimide mediated chemistry.

Specifically, 6%-7% w/v silk fibroin solution in water was reacted with diazonium salt in order to introduce carboxy groups on the tyrosine residues of silk. See Murphy et al., 29

Biomaterials 2829 (2008). The reaction product was purified by using NAP-25 (VWR International, West Chester, Pa.) desalting columns. The resulting solution was then reacted with 1M chloroacetic acid for 1 hr at room temperature under magnetic stirring. The product was purified by dialysis (MWCO 3,500) for 72 hr. The resulting solution was divided into three equal amounts.

In one part of the resulting solution, 1 g of poly-lysine hydrobromide was added, the pH of the solution was adjusted to 6.0, and then 30 mg of EDC was added. The reaction was carried out for 4 hr at room temperature under gentle magnetic stirring, and then the reaction product was purified by dialysis (MWCO 20,000) for 72 hr. In another part of the resulting solution, the same protocol was followed for obtaining the poly-glutamate derived silk fibroin. The last part of the solution was used as a control reaction, for which the above protocol was followed, without the addition of poly-amino acids.

Example 2

Characterization of Silk Fibroin-Based Ionomers

To confirm the structures of the reaction products, solutions were lyophilized, re-dissolved in deuterated water ($D_2O$) and then analyzed with a Bruker 300 MHz NMR spectrometer (Bruker, Billerica, Mass.). The $^1$H-NMR results (300 MHz $D_2O$) of the reaction products are listed as follows:

Silk fibroin: δ 0.72 (br, Valγ), 1.21 (br, Alaβ), 1.90 (br, Valβ), 2.74-2.85 (br, Asp/Tyrβ), 3.77 (m, Serβ/Glyα), 4.14-4.29 (m, Alaα/Serα), 6.61 (m, Tyrφ), 6.90 (m, Tyrφ), 7.03-7.12 (br, Pheφ).

Azo-silk fibroin: δ 0.74 (br, Valγ), 1.22 (br, Alaβ), 1.88 (br, Valβ), 2.74-2.85 (br, Asp/Tyrβ), 3.78 (m, Serβ/Glyα), 4.16-4.30 (m, Alaα/Serα), 6.63 (m, Tyrφ), 6.90 (m, Tyrφ), 7.03-7.12 (br, Pheφ), 7.05 (br, azo), 7.19 (br, azo).

Carboxy-silk fibroin: δ 0.69 (br, Valγ), 1.21 (br, Alaβ), 1.83 (br, Valβ), 2.54 (br, Asp/Tyrβ), 3.52 (s, —CH2-COOH), 3.78 (m, Serβ/Glyα), 4.15 (m, Alaα/Serα), 7.06 (br, azo), 7.18 (br, azo).

Silk fibroin-poly-lysine hydrobromide: δ 0.73 (br, Valγ), 1.27-1.29 (m, Lysγ), 1.54 (m, Lysβ/Lysδ), 2.84 (m, Lysε), 3.52 (s, —CH2-COOH), 3.73 (m, Serβ/Glyα), 4.15 (m, Lysα).

Silk fibroin-poly-glutamic acid sodium salt: δ 0.73 (br, Valγ), 1.22 (br, Alaβ), 1.52-2.00 (m, Gluβ), 2.15 (m, Gluγ), 3.52 (s, —CH2-COOH), 3.78 (m, Serβ/Glyα), 4.16 (m, Gluα).

Regarding gelation tests, solutions of the silk fibroin-PL, silk fibroin-PG and the silk fibroin control, each having a concentration of 25% w/v in water, were prepared at different pH values ranging from pH 4.0 to pH 9.0. Equal volumes of the silk fibroin-PL and silk fibroin-PG prepared at the same pH value were mixed together. Gelation/aggregation was assessed by a modified test tube inversion method. See Shu et al., 3 Biomacromol. 1304-11 (2002). Specifically, a gel (or colloid) is considered formed when there was no observation of material fluidity or liquid accumulation on the bottom of the inverted vial/tube.

Samples of colloidal gel were collected on glass slides and were analyzed by a Leica TCS SP2 Confocal Laser Scanning Microscope (Leica Microsystems, Wetzlar, Germany) in a reflectance mode. For the 3D images, 51 scans were performed. The Leica software was used to quantify the sizes of the particles by measuring the width of half of maximum pixel intensity for thirty particles.

Example 3

Cytocompatibility

For cytocompatibility assays, primary human cervical fibroblasts passage six (2 µl of $1\times10^4$ cells/slide), were added to 25 µl silk fibroin-poly-glutamate and cast onto a 35 mm glass bottom Petri dish with a 14 mm microwell (MatTek, Ashland, Mass.). Poly-lysine was then added to the Petri dish leading to an instant aggregation with cells entrapped into the silk fibroin-based ionomer composition. The composition was allowed to set for 5 min, and then 2 ml cell culture media was gently added to the composition without disturbing the composition. The plates with cell-entrapped silk composition were incubated for 72 hr at 37° C. in 5% $CO_2$. Cell viability was assessed by using a Live/Dead Viability/Cytotoxicity Kit (Invitrogen, Carlsbad, Calif.). Images were collected with a fluorescent microscope (Leica Microsystems) at 100× magnification. The viability was estimated by counting the number of viable and dead cells, respectively, in ten images acquired from different gel sections.

Example 4

Drug Release

Drug loaded silk ionomer particles were prepared by dissolving silk fibroin-PL and silk fibroin-PG in 250 µg/ml, each in doxorubicin solution (1×PBS) at pH 7.4. The final concentration of each solution was 5% w/v. Solutions of silk-poly-amino acid ionomers were then mixed together in equal volumes to yield drug-loaded particles. Samples were then washed three times in 1×PBS, pH 7.4, to remove any drug that are not bound or entrapped in the particles. Particles were then resuspended in several 500 µl 1×PBS at different pHs (i.e., pH 4.0, pH 7.0 and pH 10.0, respectively). The three vials containing particle colloid at pH 4.0, pH 7.0 and pH 10.0 were then incubated at 37° C. 50 rpm. Thereafter, particles were spun down at 2000 rpm for 5 min, and 100 µl supernatant were removed for concentration determination and replaced with fresh buffer. The loading capacity of the particles was determined by difference of emission peak intensities at 585 nm (emission frequency of doxorubicin) between the doxorubicin-containing solutions after particle formation and prior to particle formations The drug release profile was obtained by calculating the cumulative release of doxorubicin from spectrometric measurements over ten days. The amounts of released doxorubicin were calculated by using pH-dependent standard curves.

REFERENCES

Hofmann, S.; Foo, C. T.; Rossetti, F.; Textor, M.; Vunjak-Novakovic, G.; Kaplan, D. L.; Merkle, H. P.; Meinel, L. J Control Release 2006, 111, 219-27.

Lawrence, B. D.; Marchant, J. K.; Pindrus, M. A.; Omenetto, F. G.; Kaplan, D. L. Biomaterials 2009, 30, 1299-308.

Soffer, L.; Wang, X.; Zhang, X.; Kluge, J.; Dorfmann, L.; Kaplan, D. L.; Leisk, G. J Biomater Sci Polym Ed 2008, 19, 653-64.

Sofia, S.; McCarthy, M. B.; Gronowicz, G.; Kaplan, D. L. J Biomed Mater Res 2001, 54, 139-48.

Sohn, S.; Strey, H. H.; Gido, S. P. Biomacromolecules 2004, 5, 751-7.

Um, I. C.; Kweon, H. Y.; Park, Y. H.; Hudson, S. Int J Biol Macromol 2001, 29, 91-7.

Kaplan, D. L.; Adams, W. W.; Farmer, B.; Viney, C. In ACS Symposium Series; McGrath, K., Kaplan, D. L., Eds.; Birkhauser: Boston, 1994; Vol. 544, p 2-16.

Kaplan, D. L.; Melo, C. M.; Arcidiancono, S.; Fossey, S.; Senecal, K.; Muller, W. In Protein based materials; McGrath, K., Kaplan, D. L., Eds.; Birkhauser: Boston, 1998, p 103-131.

Wang, Y.; Kim, H. J.; Vunjak-Novakovic, G.; Kaplan, D. L. Biomaterials 2006, 27, 6064-82.

Bini, E.; Knight, D. P.; Kaplan, D. L. J Mol Biol 2004, 335, 27-40.

Zhou, C. Z.; Confalonieri, F.; Jacquet, M.; Perasso, R.; Li, Z. G.; Janin, J. Proteins 2001, 44, 119-22.

Jin, H. J.; Fridrikh, S. V.; Rutledge, G. C.; Kaplan, D. L. Biomacromolecules 2002, 3, 1233-9.

Wang, X.; Kluge, J. A.; Leisk, G. G.; Kaplan, D. L. Biomaterials 2008, 29, 1054-64.

Murphy, A. R.; St John, P.; Kaplan, D. L. Biomaterials 2008, 29, 2829-38.

Wang, Y.; Rudym, D. D.; Walsh, A.; Abrahamsen, L.; Kim, H. J.; Kim, H. S.; Kicker-Head, C.; Kaplan, D. L. Biomaterials 2008, 29, 3415-28.

Shi, L.; Berkland, C. Advanced Materials 2006, 18, 2315-2319.

Wang, Q.; Wang, L.; Detamore, M. S.; Berkland, C. Advanced Materials 2008, 20, 236-239.

Tanaka, K.; Kajiyama, N.; Ishikura, K.; Waga, S.; Kikuchi, A.; Ohtomo, K.; Takagi, T.; Mizuno, S. Biochim Biophys Acta 1999, 1432, 92-103.

Asakura, T.; Suita, K.; Kameda, T.; Afonin, S.; Ulrich, A. S. Magn Reson Chem 2004, 42, 258-66.

Shu, X. Z.; Liu, Y.; Luo, Y.; Roberts, M. C.; Prestwich, G. D. Biomacromolecules 2002, 3, 1304-11.

It is understood that the foregoing detailed description and example are illustrative only and are not to be taken as limitations upon the scope of the invention. Various changes and modifications to the disclosed embodiments, which will be apparent to those of skill in the art, may be made without departing from the spirit and scope of the present invention.

We claim:

1. An ionomeric gel composition comprising:
   ionomeric particles distributed in a solution to form an ionomeric gel composition, which ionomeric particles are formed by electrostatic interaction of
   a positively-charged silk fibroin, which positively-charged silk fibroin is a modified silk in that a plurality of its amino acid residues are covalently linked with a positively charged group so that its charge density is high relative to that of unmodified silk fibroin; and
   a negatively-charged silk fibroin, which negatively charged silk fibroin is a modified silk in that a plurality of its amino acid residues are covalently linked with a negatively charged group, so that its charge density is high relative to that of unmodified silk fibroin and is sufficient relative to that of the positively-charged silk fibroin to form the ionomeric particles;
   wherein electrostatic interaction is characterized in that, when the particles are exposed to an environmental stimulus selected from the group consisting of a change in pH, a change in ionic strength, a change in temperature, a change in an electrical current applied to the composition, a change on a mechanical stress as applied to the composition, and any combination thereof, the interaction is reversible so that the particles can be reversibly transformed from the gel composition into a dissociated charged silk fibroin solution, wherein the particles are distributed in the solution as an ionomeric colloid.

2. The ionomeric composition of claim 1, wherein the size of the ionomeric particle ranges from about 200 nm to about 500 nm.

3. The ionomeric composition of claim 1, wherein the composition, the particles, or both further comprise at least one active agent.

4. The ionomeric composition of claim 1, wherein each positively charged group comprises a group selected from the group consisting of positively charged polymeric amino acids, positively charged polymeric amino acid salts and any combination thereof.

5. The ionomeric composition of claim 1, wherein each negatively charged group comprises a group selected from the group consisting of negatively charged polymeric amino acids, negatively charged polymeric amino acid salts and any combination thereof.

6. The ionomeric composition of claim 1, wherein the environmental stimulus includes a change to neutral pH.

7. The ionomeric composition of claim 1, wherein the ionomeric colloid is useful as an absorbent material, a contrast agent, a diode, a tissue implant, a sensor device, a biodelivery system, or any combinations thereof.

8. The ionomeric composition of claim 1, further comprising;
   an agent to be delivered, so that the composition is a biodelivery system, or a pharmaceutically acceptable excipient, so that the composition is a pharmaceutical formulation.

9. A method of preparing a silk fibroin ionomeric gel composition, the method comprising steps of:
   providing a positively charged silk fibroin, which positively-charged silk fibroin is a modified silk in that a plurality of its amino acid residues are covalently linked with a positively charged group so that its charge density is high relative to that of unmodified silk fibroin;
   providing a negatively charged silk fibroin, which negatively charged silk fibroin is a modified silk in that a plurality of its amino acid residues are covalently linked with a negatively charged group, so that its charge density is high relative to that of unmodified silk fibroin and is sufficient relative to that of the positively-charged silk fibroin to form ionomeric particles; and
   associating the positively charged silk fibroin and the negatively charged silk fibroin via electrostatic interaction to form a gel, where the electrostatic interaction is characterized in that, when the particles are exposed to an environmental stimulus selected from the group consisting of a change in pH, a change in ionic strength, a change in temperature, a change in electrical current applied to the composition, a change in mechanical stress as applied to the composition, and any combination thereof, the interaction is reversible so that the particles can be reversibly transformed from the gel into a dissociated charged silk fibroin solution, wherein the particles are distributed in the solution as an ionomeric colloid.

10. The method of claim 9, further comprising:
   introducing at least one active agent to a solution of at least one of the charged silk fibroins.

11. The method of claim 10, wherein the step of associating is performed under conditions so that the active agent is encapsulated inside some or all of the ionomeric particles.

12. The method of claim 9, wherein the environmental stimulus includes a change to neutral pH.

13. The method of claim 10, wherein the active agent is selected from the group consisting of cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, and drugs.

14. The method of claim 13, wherein the active agent is hydrophilic.

15. The method of claim 9, wherein the charged silk fibroins are formed by a method comprising steps of:
   modifying a first silk fibroin and a second silk fibroin to enrich fibroin functional groups on each of the first and second silk fibroins to react with a charged polymeric amino acid;
   reacting a portion of the first modified silk fibroin with a positively charged polymeric amino acid to form a positively charged silk fibroin; and
   reacting a portion of the second modified silk fibroin with a negatively charged polymeric amino acid to form a negatively charged silk fibroin.

16. The method of claim 15, wherein the modifying is by means of a reaction selected from the group consisting of carbodiimide coupling reaction, diazonium coupling reaction, and charge-charge interaction.

17. The method of claim 15, wherein the reacting is selected from the group consisting of carbodiimide coupling reaction, diazonium coupling reaction, and charge-charge interaction.

18. The ionomeric composition of claim 1, wherein the ionomeric composition is pH-dependent.

19. The ionomeric composition of claim 1, wherein a core of the silk fibroin ionomeric particle is hydrophilic.

20. The ionomeric composition of clam 4, wherein the positively charged polymeric amino acids are selected from the group consisting of polylysine, polyarginine, polyhistidine, and any combination thereof.

21. The ionomeric composition of clam 5, wherein the negatively charged polymeric amino acids are selected from the group consisting of polyglutamate, polyaspartate, and any combination thereof.

22. The ionomeric composition of claim 18, further comprising an active agent, wherein at neutral pH, the active agent is released from the composition for a period of at least about 5 months, or at acidic pH, the active agent is released from the composition for a period of at least about 1 month, or at basic pH, the active agent is released from the composition for a period of at least about 2 months.

* * * * *

UNITED STATES PATENT AND TRADEMARK OFFICE
CERTIFICATE OF CORRECTION

| | | |
|---|---|---|
| PATENT NO. | : 9,603,971 B2 | Page 1 of 1 |
| APPLICATION NO. | : 13/582903 | |
| DATED | : March 28, 2017 | |
| INVENTOR(S) | : David L. Kaplan and Monica A. Serban | |

It is certified that error appears in the above-identified patent and that said Letters Patent is hereby corrected as shown below:

In the Claims

Column 32, Line 13 (Claim 20): Please replace the text "The ionomeric composition of clam 4, wherein the" with -- The ionomeric composition of claim 4, wherein the --

Column 32, Line 17 (Claim 21): Please replace the text "The ionomeric composition of clam 5, wherein the" with -- The ionomeric composition of claim 5, wherein the --

Signed and Sealed this
Seventh Day of August, 2018

Andrei Iancu
*Director of the United States Patent and Trademark Office*